(12) United States Patent
Kothari et al.

(10) Patent No.: US 9,358,207 B2
(45) Date of Patent: *Jun. 7, 2016

(54) FLASHMELT ORAL DOSAGE FORMULATION

(71) Applicant: OTSUKA PHARMACEUTICAL CO., LTD., Tokyo (JP)

(72) Inventors: Sanjeev H. Kothari, Princeton, NJ (US); Divyakant S. Desai, West Windsor, NJ (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/938,706

(22) Filed: Jul. 10, 2013

(65) Prior Publication Data

US 2013/0296337 A1    Nov. 7, 2013

Related U.S. Application Data

(63) Continuation of application No. 13/108,193, filed on May 16, 2011, now Pat. No. 8,518,421, which is a continuation of application No. 12/558,813, filed on Sep. 14, 2009, now abandoned, which is a continuation (Continued)

(51) Int. Cl.
*A61K 9/00* (2006.01)
*A61K 9/20* (2006.01)
*A61K 31/496* (2006.01)

(52) U.S. Cl.
CPC .............. *A61K 9/0056* (2013.01); *A61K 9/2009* (2013.01); *A61K 9/2018* (2013.01); *A61K 9/2027* (2013.01); *A61K 9/2054* (2013.01); *A61K 9/2059* (2013.01); *A61K 31/496* (2013.01)

(58) Field of Classification Search
CPC . A61K 31/496; A61K 9/0056; A61K 9/2009; A61K 9/2018; A61K 9/2027; A61K 9/2054; A61K 9/2059
See application file for complete search history.

(56) References Cited

U.S. PATENT DOCUMENTS 3,622,677 A * 11/1971 Short et al. ............... 514/778
4,906,478 A *  3/1990 Valentine et al. .......... 424/682

(Continued)

FOREIGN PATENT DOCUMENTS

WO        WO 98/03064        *  1/1998  ............... A61K 9/14

OTHER PUBLICATIONS

Sasa et al., "Unique Pharmacological Profile of a Novel Antipsychotic Drug, Aripiprazole (OPC-14597)" CNS Drug Reviews, 1997, vol. 3, No. 1, pp. 24-33.*

*Primary Examiner* — Aradhana Sasan
(74) *Attorney, Agent, or Firm* — Finnegan, Henderson, Farabow, Garrett & Dunner LLP

(57) ABSTRACT

There is provided granules for the production of flash-melt pharmaceutical oral dosage forms. In addition to one or more medicaments, the granules are composed of an excipient combination consisting of a superdisintegrant, a dispersing agent, a distributing agent, and a binder and may also include other conventional ingredients such as sweetening and flavoring agents. The subject granules are advantageous in that they are stable and can be prepared without the aid of solvents and without the need for special environments or handling. Dosage forms, especially tablets, prepared therefrom on conventional equipment disintegrate in the mouth in under about twenty five seconds.

20 Claims, 5 Drawing Sheets

Related U.S. Application Data of application No. 12/056,410, filed on Mar. 27, 2008, now abandoned, which is a continuation of application No. 10/979,556, filed on Nov. 2, 2004, now abandoned, which is a continuation of application No. 10/920,851, filed on Aug. 18, 2004, now abandoned, which is a continuation of application No. 09/973,226, filed on Oct. 9, 2001, now abandoned, which is a continuation-in-part of application No. 09/589,340, filed on Jun. 7, 2000, now abandoned, which is a continuation-in-part of application No. 09/547,948, filed on Apr. 12, 2000, now abandoned.

(56) References Cited

U.S. PATENT DOCUMENTS

| | | | | |
|---|---|---|---|---|
| 5,587,172 | A | * | 12/1996 | Cherukuri et al. ............ 424/401 |
| 8,518,421 | B2 | * | 8/2013 | Kothari et al. ................ 424/400 |

* cited by examiner

FLASHMELT ORAL DOSAGE FORMULATION

CROSS REFERENCE TO RELATED APPLICATIONS

This application is a continuation of Ser. No. 13/108,193 filed May 16, 2011, now allowed, which is a continuation of Ser. No. 12/558,813 filed Sep. 14, 2009, now abandoned, which is a continuation of U.S. application Ser. No. 12/056,410 filed Mar. 27, 2008, now abandoned, which is a continuation of U.S. application Ser. No. 10/979,556 filed Nov. 2, 2004, now abandoned, which is a continuation of U.S. application Ser. No. 10/920,851 filed Aug. 18, 2004, now abandoned, which is a continuation of U.S. application Ser. No. 09/973,226 filed Oct. 9, 2001, now abandoned, which is a continuation-in-part of U.S. application Ser. No. 09/589,340 filed Jun. 7, 2000, now abandoned, which is a continuation in-part of U.S. application Ser. No. 09/547,948 filed Apr. 12, 2000, now abandoned.

FIELD OF THE INVENTION

The present invention relates to a formulation for solid pharmaceutical oral dosage forms that rapidly disperses in the mouth.

BACKGROUND OF THE INVENTION

There are a variety of solid pharmaceutical dosage forms that rapidly dissolve or disintegrate in a glass of water or in the gastrointestinal tract. Such dosage forms have been known in the art for many years. The obvious advantages of the convenience of carrying dosage forms that will dissolve or effervesce in water to release medicaments are well known. The therapeutic need of having an oral dosage form that will rapidly dissolve or disintegrate in the mouth for situations where immediate medication is necessary and water is not available has long been recognized.

Initially, a distinction must be drawn between flash-melt dosage forms and rapidly disintegrating dosage forms. The former are intended to dissolve or disintegrate in the mouth of the patient in less than one minute whereas the latter are intended for primary dissolution or disintegration within 3 to 20 minutes in the acidic medium of the stomach or a container of water. The recognized test for rapidly disintegrating dosage forms is disintegration time in 0.1 N hydrochloric acid. Those of ordinary skill in the art will appreciate that the requirements for formulating dosage forms to meet these criteria must necessarily be different since the conditions, particularly pH, in the mouth and the stomach are quite different. More importantly, the time in which a dosage form must dissolve or disintegrate in the mouth is necessarily much shorter than in the stomach with the obvious exception of dosage forms, e.g. lozenges, that are specifically formulated to slowly dissolve in the mouth.

Another consideration common to most if not all dosage form formulations intended for flash-melt or rapid disintegration is the need to take precautions in the preparation, packaging, handling and storing of the finished dosage forms since they tend to be both hygroscopic and friable. Dosage forms dependent on effervescence to promote their disintegration are particularly susceptible to moisture and must be packaged with special wrapping, stoppers, packets of drying agent and the like.

Regardless of such potential problems, there is still an acute need for dosage forms that can rapidly dissolve or disintegrate for the obvious benefits of having a therapeutic dosage of the medicament contained therein available for absorption in a very short time. In addition to the benefits of rapid availability, flash-melt dosage forms are advantageous for administration of medicaments to patients such as the very young, the elderly, the non-compliant and those with a physical impairment that makes it difficult if not impossible to swallow an intact dosage form. Flash-melt dosage forms are further a convenience for situations where portable water may not be readily available or desirable. Medicaments amenable to such dosage forms would include sedatives, hypnotics, antipsychotics, motion sickness medication, mild stimulants such as caffeine and the like.

Those of ordinary skill in the art are aware that there are two basic compounding concepts recognized for the preparation of rapidly dissolving/disintegrating dosage forms. The first of these, particularly suited for the preparation of flash-melt dosage forms, is freeze drying wherein a cake or wafer is prepared from a freeze-dried solution or suspension of medicament and suitable excipients in water or other solvents. Such wafers dissolve very rapidly on the tongue, i.e. within about ten seconds, due to a combination of a high affinity for moisture resulting from the freeze drying process and a very high porosity, which promotes rapid ingress of saliva. While such dosage forms are capable of rapid disintegration/dissolution in the mouth, the freeze drying process suffers from several disadvantages, primary among which is the fact that a solution or a stable suspension of the medicament must be formed before it can be freeze dried. While not always the case, typically such solutions are aqueous and, therefore, not suited to formulating medicaments sensitive to water. The process itself is typically laborious and time-consuming. Finally, the resultant dosage forms, in addition to being hygroscopic, tend to be very soft and, therefore, require special moisture- and impact-resistant packaging and require careful handling prior to administration.

The second major technology utilized in the manufacture of rapidly disintegrating dosage forms is based on special grades of sugars such as mannitol, sorbitol and the like in combination with superdisintegrants. The latter are excipients that are characterized by a special wicking capacity to channel water into the interior of the dosage form, or by rapid swelling in water, both of which act to hasten disintegration. It is also known to enhance dissolution of dosage forms by the inclusion of effervescent combinations, typically sodium bicarbonate and a weak acid, such as citric acid. As noted above, effervescent formulations require special moisture resistant packaging as even very small levels of moisture may be sufficient to initiate the effervescent reaction. Techniques, such as fluidized bed granulation, are recognized as being useful in the preparation of such formulations. Too often, however, such technologies require a specific, very costly plant including special handling equipment, controlled-humidity environments and the like. In spite of such measures, dosage forms produced by such techniques typically require moisture resistant packaging, the need to include in the packaging packets or capsules of moisture absorbing agents and the like.

An example of a teaching of the incorporation of super disintegrants in dosage form formulations to enhance dissolution is WO 98/03064, FMC Corporation. It is disclosed therein that, for cost considerations, up to 90% of a group of super disintegrants including cross-linked cellulose, cross-linked carboxymethyl cellulose, cross-linked starch, croscarmellose alkali metal salt, crospovidone, alkali metal starch glycolate and the like can be replaced by a co-disintegrant. Included among the latter group are natural diatomaceous silica, a synthetic hydrous alkaline earth metal calcium silicate and a porous hydrophilic zeolite. The weight ratio of super disintegrant to co-disintegrant is stated as from 4:1 to 1:10, preferably 2-1:1. There is no indication of any recognition of benefits to be derived from the formulation other than the obvious consideration of cost savings since the co-disintegrants are less expensive and the combination is stated to accomplish the desired results.

In contrast, Japanese patent 10114655, Kyowa Hakko Kogyo KK discloses a formulation intended for rapid dissolution in the stomach that can contain up to 30% by weight of a superdisintegrant, such as crospovidone or hydroxypropylcellulose, croscarmellose and the like and up to 30% of a neutral or basic ingredient including magnesium aluminum metasilicate, calcium silicate, a phosphoric acid salt or a metal hydroxide. The dosage form is intended for medicaments that produce a gel at acidic pH.

There are numerous other examples of specific formulations that utilize one or more of the techniques or mechanisms discussed above. For the most part, however, they also possess one or more of the enumerated disadvantages to some degree, e.g. it is difficult or expensive to produce dosage forms by such techniques, the resulting dosage forms are friable or are sensitive to environmental factors such as moisture. There continues to be the need for a formulation that mitigates or eliminates these disadvantages, yet yields a flash-melt dosage form that will disintegrate in the mouth within about 25 seconds. Such formulations are provided in accordance with the present invention.

SUMMARY OF THE INVENTION

According to a first embodiment of the present invention is provided a flash-melt pharmaceutical dosage form comprising a medicament, a superdisintegrant, a dispersing agent and a binder wherein said medicament is aripiprazole, entecavir, cefprozil, pravastatin, captopril, gatifloxacin, desquinolone, omapatrilat or irbesartan and wherein said dispersing agent is calcium silicate, magnesium trisilicate or silicic acid.

According to a first series of embodiments of the present invention are provided flash-melt pharmaceutical dosage forms as described herein wherein greater than 50% of said dispersing agent by weight is comprised of calcium silicate.

According to other embodiments of the present invention are provided flash-melt pharmaceutical dosage forms as described herein wherein greater than 80% of said dispersing agent by weight is comprised of calcium silicate.

According to other embodiments of the present invention are provided flash-melt pharmaceutical dosage forms as described herein wherein said dispersing agent is calcium silicate.

According to other embodiments of the present invention are provided flash-melt pharmaceutical dosage forms as described herein wherein said dispersing agent comprises from about 20 to about 70 percent by weight of said dispersing agent based on the total weight of said dosage form.

According to other embodiments of the present invention are provided flash-melt pharmaceutical dosage forms as described herein wherein said dispersing agent comprises from about 35 to about 45 percent by weight of said dispersing agent based on the total weight of said dosage form.

According to other embodiments of the present invention are provided flash-melt pharmaceutical dosage forms as described herein wherein said calcium silicate is crystalline.

According to other embodiments of the present invention are provided flash-melt pharmaceutical dosage forms as described herein wherein said calcium silicate is amorphous.

According to other embodiments of the present invention are provided flash-melt pharmaceutical dosage forms as described herein wherein said calcium silicate is ortho-, meta- or alpha triclinic-calcium silicate.

According to other embodiments of the present invention are provided flash-melt pharmaceutical dosage forms as described herein wherein said calcium silicate is alpha triclinic-calcium silicate.

According to other embodiments of the present invention are provided flash-melt pharmaceutical dosage forms as described herein wherein said calcium silicate is comprised of a combination of alpha triclinic-calcium silicate and at least one other pharmaceutical grade of calcium silicate wherein said alpha triclinic-calcium silicate comprises from about 10% to about 90% by weight of said combination.

According to other embodiments of the present invention are provided flash-melt pharmaceutical dosage forms as described herein wherein said calcium silicate has a surface area of 1.0 $m^2$/gm to 210 $m^2$/gm, bulk density of 0.075 g/cc to 0.90 g/cc, true density of 1.70 g/cc to 2.90 g/cc and volatile content of less than 1% to 14% w/w.

According to other embodiments of the present invention are provided flash-melt pharmaceutical dosage forms as described herein wherein said calcium silicate is alpha triclinic calcium silicate that has a surface area of about 1.3 $m^2$/gm, bulk density of about 0.63 g/cc, true density of about 2.90 g/cc and volatile content of less than 1% w/w.

According to other embodiments of the present invention are provided flash-melt pharmaceutical dosage forms as described herein wherein said calcium silicate is ortho crystalline calcium silicate that has a surface area of about 0.98 $m^2$/gm, bulk density of about 0.492 g/cc, true density of about 3.252 g/cc and volatile content of less than 1% w/w.

According to other embodiments of the present invention are provided flash-melt pharmaceutical dosage forms as described herein wherein said calcium silicate is meta crystalline calcium silicate that has a surface area of about 2.5 $m^2$/gm, bulk density of about 0.867 g/cc, true density of about 2.940 g/cc and volatile content of less than 1% w/w.

According to other embodiments of the present invention are provided flash-melt pharmaceutical dosage forms as described herein wherein said calcium silicate is crystalline calcium silicate that has a surface area of about 90.4 $m^2$/gm, bulk density of about 0.094 g/cc, true density of about 2.596 g/cc and volatile content of less than 1% w/w.

According to other embodiments of the present invention are provided flash-melt pharmaceutical dosage forms as described herein wherein said calcium silicate is amorphous calcium silicate that has a surface area of about 191.3 $m^2$/gm, bulk density of about 0.120 g/cc, true density of about 2.314 g/cc and volatile content of about less than 14% w/w.

According to other embodiments of the present invention are provided flash-melt pharmaceutical dosage forms as described herein wherein said calcium silicate is amorphous calcium silicate that has a surface area of about 103.0 $m^2$/gm, bulk density of about 0.130 g/cc, true density of about 1.702 g/cc and volatile content of about less than 14% w/w.

According to other embodiments of the present invention are provided flash-melt pharmaceutical dosage forms as described herein wherein said calcium silicate is amorphous calcium silicate that has a surface area of about 209 $m^2$/gm, bulk density of about 0.075 g/cc, true density of about 2.035 g/cc and volatile content of about less than 14% w/w.

According to other embodiments of the present invention are provided flash-melt pharmaceutical dosage forms as described herein wherein said medicament comprises not more than about 30 percent by weight of said medicament based on the total weight of said dosage form.

According to other embodiments of the present invention are provided flash-melt pharmaceutical dosage forms as described herein wherein said medicament comprises not more than about 15 percent by weight of said medicament based on the total weight of said dosage form.

According to other embodiments of the present invention are provided flash-melt pharmaceutical dosage forms as described herein wherein said medicament is selected from the group consisting of aripiprazole, entecavir, cefprozil, pravastatin, captopril, gatifloxacin, desquinolone, omapatrilat and irbesartan.

According to other embodiments of the present invention are provided flash-melt pharmaceutical dosage forms as described herein wherein said medicament is aripiprazole.

According to other embodiments of the present invention are provided flash-melt pharmaceutical dosage forms as described herein wherein said superdisintegrant agent comprises from about 3 to about 15 percent by weight of said superdisintegrant agent based on the total weight of said dosage form.

According to other embodiments of the present invention are provided flash-melt pharmaceutical dosage forms as described herein wherein said superdisintegrant agent comprises from about 4 to about 10 percent by weight of said superdisintegrant agent based on the total weight of said dosage form.

According to other embodiments of the present invention are provided flash-melt pharmaceutical dosage forms as described herein wherein said superdisintegrant agent comprises from about 4 to about 8 percent by weight of said superdisintegrant agent based on the total weight of said dosage form.

According to other embodiments of the present invention are provided flash-melt pharmaceutical dosage forms as described herein wherein said superdisintegrant agent comprises from about 5 to about 7 percent by weight of said superdisintegrant agent based on the total weight of said dosage form.

According to other embodiments of the present invention are provided flash-melt pharmaceutical dosage forms as described herein wherein said superdisintegrant agent comprises from about 8 to about 12 percent by weight of said superdisintegrant agent based on the total weight of said dosage form.

According to other embodiments of the present invention are provided flash-melt pharmaceutical dosage forms as described herein wherein said superdisintegrant agent comprises from about 9 to about 10 percent by weight of said superdisintegrant agent based on the total weight of said dosage form.

According to other embodiments of the present invention are provided flash-melt pharmaceutical dosage forms as described herein wherein said superdisintegrant agent is crospovidone, croscarmellose sodium, sodium starch glycolate, low-substituted hydroxypropyl cellulose or pregelatinized starch.

According to other embodiments of the present invention are provided flash-melt pharmaceutical dosage forms as described herein wherein said superdisintegrant agent is crospovidone or croscarmellose sodium.

According to other embodiments of the present invention are provided flash-melt pharmaceutical dosage forms as described herein wherein said superdisintegrant agent is crospovidone and croscarmellose sodium.

According to other embodiments of the present invention are provided flash-melt pharmaceutical dosage forms as described herein, wherein based on the total weight of said dosage form, said crospovidone comprises from about 6 to about 8 percent by weight of said crospovidone and said croscarmellose sodium comprises from about 2 to about 4 percent by weight of said croscarmellose sodium.

According to other embodiments of the present invention are provided flash-melt pharmaceutical dosage forms as described herein wherein said distributing agent comprises from about 1 to about 10 percent by weight of said distributing agent based on the total weight of said dosage form.

According to other embodiments of the present invention are provided flash-melt pharmaceutical dosage forms as described herein wherein said distributing agent comprises from about 1.5 to about 3 percent by weight of said distributing agent based on the total weight of said dosage form.

According to other embodiments of the present invention are provided flash-melt pharmaceutical dosage forms as described herein wherein said distributing agent is amorphous silica, fumed silica, diatomaceous earth, talc, kaolin or magnesium aluminum trisilicate.

According to other embodiments of the present invention are provided flash-melt pharmaceutical dosage forms as described herein wherein said distributing agent comprises from about 10 to about 50 percent by weight of said binder based on the total weight of said dosage form.

According to other embodiments of the present invention are provided flash-melt pharmaceutical dosage forms as described herein wherein said distributing agent comprises from about 12 to about 20 percent by weight of said binder based on the total weight of said dosage form.

According to other embodiments of the present invention are provided flash-melt pharmaceutical dosage forms as described herein wherein said binder is microcrystalline cellulose, hydroxypropyl cellulose, ethyl cellulose, lactose, mannitol or calcium phosphate.

Yet other embodiments or aspects of the present invention reside in the combination of one or more of the embodiments or aspects described herein.

Yet other embodiments or aspects of the present invention are described below.

DETAILED DESCRIPTION OF THE INVENTION

Figure 1:
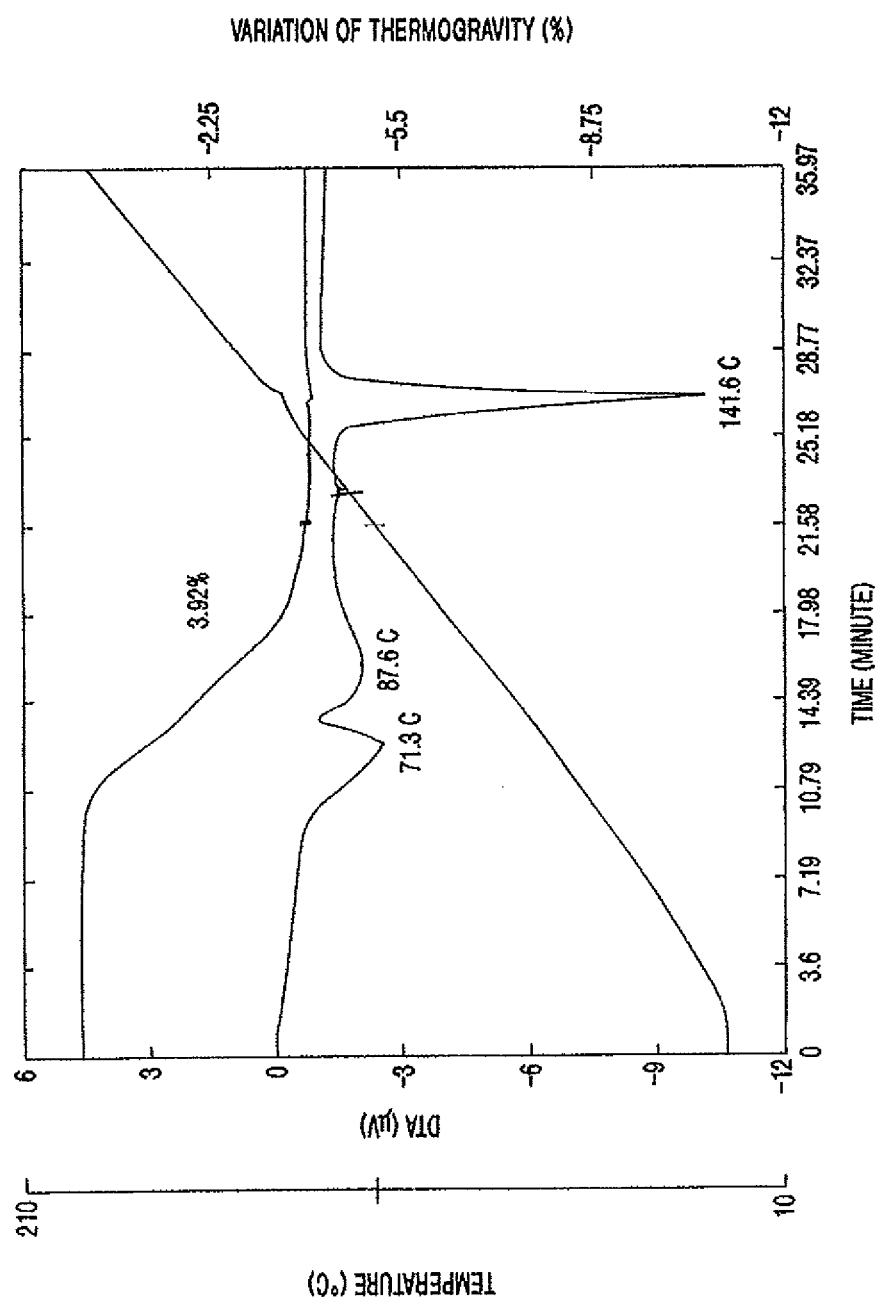
FIG. 1 shows the endothermic curve for the aripiprazole hydrate (grains) of the present invention.

As used herein the terms "a medicament", "a superdisintegrant", "a dispersing agent", "a distributing agent" or "a binder" means that one or more of agents belonging to each class may be suitably employed in the present invention unless otherwise specified. Furthermore, if agents belonging to a particular class are referred to in the alternative, it is understood that one or more of said agents may be suitably employed. Thus for example, two or more superdisintegrants may be employed unless otherwise specified. The flash-melt pharmaceutical dosage forms the present invention may be prepared by dry granulation of the excipients with the medicament and suitable conventional ingredients, such as flavoring and sweetening agents, without the use of any solvent, to form stable granules that can be readily compressed into dosage forms on conventional equipment without the need for special handling techniques.

The active medicament may comprise up to about 30% by weight, particularly up to about 15% by weight, of the formulation, depending on the amount required for a therapeutically effective dosage and factors such as its capacity to be directly granulated, the amount of flavoring/sweetening agents required to mask the taste or bitterness thereof and the like. It is within the scope of the present invention to utilize medicaments that are coated for taste or other reason in the subject formulations provided that the coatings do not interfere with either the compounding or the disintegration of the tablets.

Suitable superdisintegrants include crospovidone, croscarmellose sodium, sodium starch glycolate, low-substituted hydroxypropylcellulose, pregelatinized starch and the like. Crospovidone can be utilized in large amounts without causing a formulation containing it to have a propensity to gel.

Suitable dispersing agents, also sometimes referred to in the art as anticaking agents, include calcium silicate-Mho, meta and alpha triclinic forms thereof, magnesium trisilicate-ortho and meta forms thereof and silicic acid. Calcium silicate is the preferred dispersing agent. Particularly preferred is a crystalline alpha triclinic calcium silicate, commercially available from Aldrich Chemical Company which meets the following specifications: 1.3 $m^2$/gm surface area; 0.63 g/cc bulk density; 2.90 g/cc true density; and <1% w/w volatiles. Also particularly preferred is a crystalline alpha triclinic calcium silicate, commercially available from J.M. Huber Inc., Tomita Pharmaceutical Co., Aldrich Chemical Company which meets the following specifications: 1.0 to 15 $m^2$/gm surface area; 0.50 to 0.63 g/cc bulk density; 2.40 to 2.90 g/cc true density; and <1% w/w volatiles. A variety of pharmaceutical grades of calcium silicate available from other vendors, as shown in Table 1, have also been found to produce satisfactory flash-melt dosage forms as well. These include ortho and meta forms of calcium silicate available from Alfa-Aesar, synthetic calcium silicates Micro-cel C and Micro-cel E, available from Celite Corp, Hubersorb 600 NF and Hubersorb 250 NF available from J.M. Huber Corp, and combinations of various grades thereof. These products have been found to cover the following range of specifications for calcium silicate: 1.0 $m^2$/gm to 210 $m^2$/gm surface area; 0.075 g/cc to 0.90 g/cc bulk density; 1.70 g/cc to 2.90 g/cc true density; and <1% to 14% w/w volatiles. Table 1 lists the individual specifications for each of the materials obtained from the vendors listed above.

TABLE 1

| Source | Description | Surface area $m^2$/gm | Bulk Density g/cc (±s.d.) | True Density g/cc | Volatiles (% w/w) |
|---|---|---|---|---|---|
| Aldrich | CaSiO3 <200mesh (crystalline, alpha triclinic) | 1.3 | 0.627 (0.020) | 2.934 | 0.50 |
| Alfa Aesar | 2CaO•SiO2 (crystalline, ortho) | 0.98 | 0.492 (0.003) | 3.252 | 0.02 |

TABLE 1-continued

| Source | Description | Surface area $m^2$/gm | Bulk Density g/cc (±s.d.) | True Density g/cc | Volatiles (% w/w) |
|---|---|---|---|---|---|
| Alfa Aesar | CaSiO3 (crystalline, meta) | 2.5 | 0.867 (0.009) | 2.940 | 0.50 |
| Celcite | Micro-cel E (crystalline) | 90.4 | 0.094 (0.006) | 2.596 | 0.94 |
| Celcite | Micro-cel C (amorphous) | 191.3 | 0.120 (0.006) | 2.314 | 5.11 |
| JM Huber | Hubersorb 250NF (amorphous) | 103.0 | 0.130 (0.008) | 1.702 | 9.90 |
| JM Huber | Hubersorb 600NF (amorphous) | 209 | 0.075 (<0.001) | 2.035 | 13.8 |

Alpha triclinic calcium silicate is advantageously combined in the subject formulations with at least one other pharmaceutical grade of calcium silicate wherein the alpha triclinic form would comprise from about 10% to about 90% by weight of the combination. In contrast to its use in conventional tabletting formulations, it is considered unexpected that the dispersing agent, i.e. calcium silicate, is the primary constituent of the excipient combination of the subject formulations since it is generally recognized by those of ordinary skill in the art as being poorly compressible.

Examples of suitable distributing agents for the excipient combination of the subject formulations include amorphous silica, fumed silica, diatomaceous earth, talc, kaolin, magnesium aluminum trisilicate and the like.

Suitable binders are those that also function as a wicking or distributing agent in that they act to promote water intake into dosage forms made therefrom. Suitable binders include carbohydrates such as, microcrystalline cellulose, hydroxypropyl cellulose, ethyl cellulose, starch, lactose, and also, mannitol and calcium phosphate. Microcrystalline cellulose is commercially available as Avicel® PH (pharmaceutical grade) from FMC Corporation, Philadelphia, Pa., particularly Avicel® PH 101, PH 102, PH 103, PH 112, PH 200, PH 301, PH 302 and Ceolus. Microcrystalline cellulose is also available from Mendell, Penwest Company, Patterson, N.Y., as Emcocel® 90M and Emcocel® 50M, which could be used satisfactorily.

The formulations of the present invention may contain other conventional ingredients found in similar preparations known in the art and recognized as approved for use in preparations to be taken into the body. These would include, for example, natural and artificial flavors, polyols such as mannitol, sorbitol, maltitol and xylitol, artificial sweetening agents such as, N-α-L-Aspartyl-L-phenylalanine 1-methyl ester (aspartame) and 6-methyl-3,4-dihydro-1,2,3-oxathiazin-4(3H)-one-2,2-dioxide, particularly the potassium salt thereof (acesulfame K), flavor adjuncts such as tartaric acid, tabletting lubricants, such as magnesium stearate, and the like. Those skilled in the art of pharmaceutical compounding will appreciate that the amount of flavoring and sweetening agents, if any, present in the formulations of the present invention will be directly proportional to the taste or bitterness of the medicament. The flavoring and sweetening agents do not serve to coat the medicament, but are adequate to mask the objectionable taste of the medicaments in homogeneous admixture therewith. In general, the total of such conventional ingredients will not exceed about 32 percent, preferably from about 25 to about 30 percent by weight based on the total weight of the formulation.

The medicament in the formulations of the present invention typically will not exceed about 30 percent by weight, preferably from about 1 to about 15 percent by weight of the formulation. Those of ordinary skill in the art will appreciate that the physical characteristics of the medicament itself, i.e. its particle size and morphology, will directly influence its limiting content in the subject formulations. Clearly, there has to be sufficient medicament in the dosage form produced form the subject formulations to provide a therapeutically effective dosage. While solid dosage forms can be prepared from the formulations of the present invention by any recognized technique, including wet granulation, it is a particular advantage that the formulations can be dry granulated without the use of specialized equipment and conditions, thereby making them suitable for the formulation of medicaments that are sensitive to moisture and high temperatures.

Examples of medicaments that can be formulated into flash-melt tablets in accordance with the present invention include, without intended limitation, antihistamines, anti-motion sickness agents, analgesics, anti-inflammatory agents, antibiotics, cholesterol lowering agents, anti-anxiety agents, anti-hypertensives, anti-cancer agents, hypnotics, anti-ulcer agents, coronary dilators, antivirals, anti-psychotics, anti-depressants, neuromuscular agents, anti-diarrheals, hypoglycemic agents, thyroid suppressors, anabolic agents, antisposmodics, antimigraine agents, diuretics, stimulants, decongestants, uterine relaxants, anti-arrhythmics, male erectile dysfunction compounds, Maxi-K channel openers or neuroprotective agents for the treatment of stroke or Alzheimer's disease and therapeutically appropriate combinations thereof. Specific therapeutic agents falling into the foregoing categories include, again without intended limitation, aripiprazole, ibuprofen, aspirin, acetaminophen, chlorpheniramine maleate, psuedoephedrine, diphenhydramine HCl, ranitidine, phenylpropanolamine, cimetidine, loperamide, meclizine, caffeine, entecavir, cefprozil, melatonergic agonists, pravastatin, captopril, fosinopril, irbesartan, omapatrilat, gatifloxacin and desquinolone and therapeutically appropriate combinations thereof.

As stated above, a decided advantage of the formulation of the present invention is that it can be dry-granulated into stable, fine granules that can be directly compressed into pharmaceutically elegant flash-melt oral dosage forms, e.g. tablets, caplets, wafers and the like. Preferably, the granules for flash-melt dosage forms in accordance with the present invention are formed in two steps. The process comprises initially forming granules, referred to herein as the intragranulation, by blending all of the medicament, the dispersing agent, (distributing agent), other conventional ingredients as described above and a portion of each of the superdisintegrant, binder and tabletting lubricant together in a suitable mixer to assure uniform distribution throughout. A conventional V-blender is a preferred apparatus for this step. While a minor portion of the dispersing agent may be omitted from the intragranulation, it is preferred that all be incorporated therein. The blended mixture is then compacted in a conventional roller compactor having an orifice such that the compacts thereof are in the form of ribbons. Alternately, a slugging process can be used. The compacts from the roller compactor or the slugs from the slugger are passed through a fine screen, e.g. a 30 mesh (600 microns) screen, thereby breaking them into granules between about 150 and 400 microns in size. The intragranulation granules thus-prepared are thereafter blended in a suitable mixer with the remaining ingredients, i.e., superdisintegrant, binder and lubricant, referred to herein as the extragranulation ingredients, to form a final blend that can be directly compressed into pharmaceutical dosage forms utilizing conventional equipment such as a tablet press. Rather than directly compress the final blend upon formation, since it is stable, it can be stored and subsequently pressed into dosage forms at a later time. It is a decided advantage of particular aspects of the subject invention that these operations are carried out without the need to resort to special handling such as taking precautions against any moisture coming in contact with the ingredients or the granules, and without the use of specially controlled temperature and humidity conditions.

The intragranulation comprises from about 80 to 99, preferably from about 85 to 95, most preferably about 90, percent by weight of the final blend. Based on the weight of the final blend, the intragranulation preferably comprises up to about 30 percent by weight, preferably from about 6 to 20 percent by weight, of the binder, up to about 5 percent by weight, preferably from about 2 to 4 percent by weight, of the superdisintegrant, and all of the dispersing agent and the distributing agent. The binder and superdisintegrant are divided between the intragranulation and the extragranulation ingredients in weight ratios of approximately 2:1 to 4:1 for the binder and 0.5:2.0 to 2.0:0.5 for the superdisintegrant. The conventional tabletting lubricant is divided approximately equally between the intragranulation and the extragranulation ingredients.

The final blend is formed by mixing the intragranulation and the extragranulation components of the excipient combination, adding the remaining tabletting lubricant thereto and blending until uniform. Alternatively, a direct compression approach can be utilized in which all of the ingredients with the exception of the tabletting lubricant are mixed in a suitable blender, such as a conventional V-blender, by geometrically building the entire mass of the formulation via sequential blending for three minutes after each addition, and finally adding the lubricant to the mixture after all other ingredients have been blended.

Tablets compressed on a conventional tablet press from the final blend obtained from either a one-step granulation or a direct compression blend, were pharmaceutically elegant and disintegrated in water within ten seconds. A tablet is considered as disintegrated when it has totally broken down to granules and there are no discernible lumps remaining. Since the medicament is not intimately bound to any of the ingredients of the formulation, it is released within the same time period. Another advantage of particular aspects of the subject formulations is that dosage forms can be manufactured therefrom which are robust and, hence, avoid the need for specialized unit dose packaging and careful handling during manufacture or use as is often the case with present dosage forms. The dosage forms prepared from formulations of particular aspects of the present invention can be packaged in conventional blister packs or in HDPE bottles.

It is understood that various other embodiments and modifications in the practice of the invention will be apparent to, and can be readily made by, those of ordinary skill in the art without departing form the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the art to which the invention pertains. The invention is further described with reference to the following experimental work.

Means of manufacturing aripiprazole drug substance for formulating according to the present flashmelt invention may be performed as follows.

Aripiprazole Hydrate

The aripiprazole hydrate (grains) of the present invention have the physicochemical properties given in (1)-(5) below. This aripiprazole hydrate is described hereinafter as "Aripiprazole Hydrate A".

(1) It has an endothermic curve which is substantially the same as the thermogravimetric/differential thermal analysis (heating rate 5° C./min) endothermic curve shown in FIG. 1. Specifically, it is characterized by the appearance of a small peak at about 71° C. and a gradual endothermic peak around 60° C. to 120° C.

Figure 2:
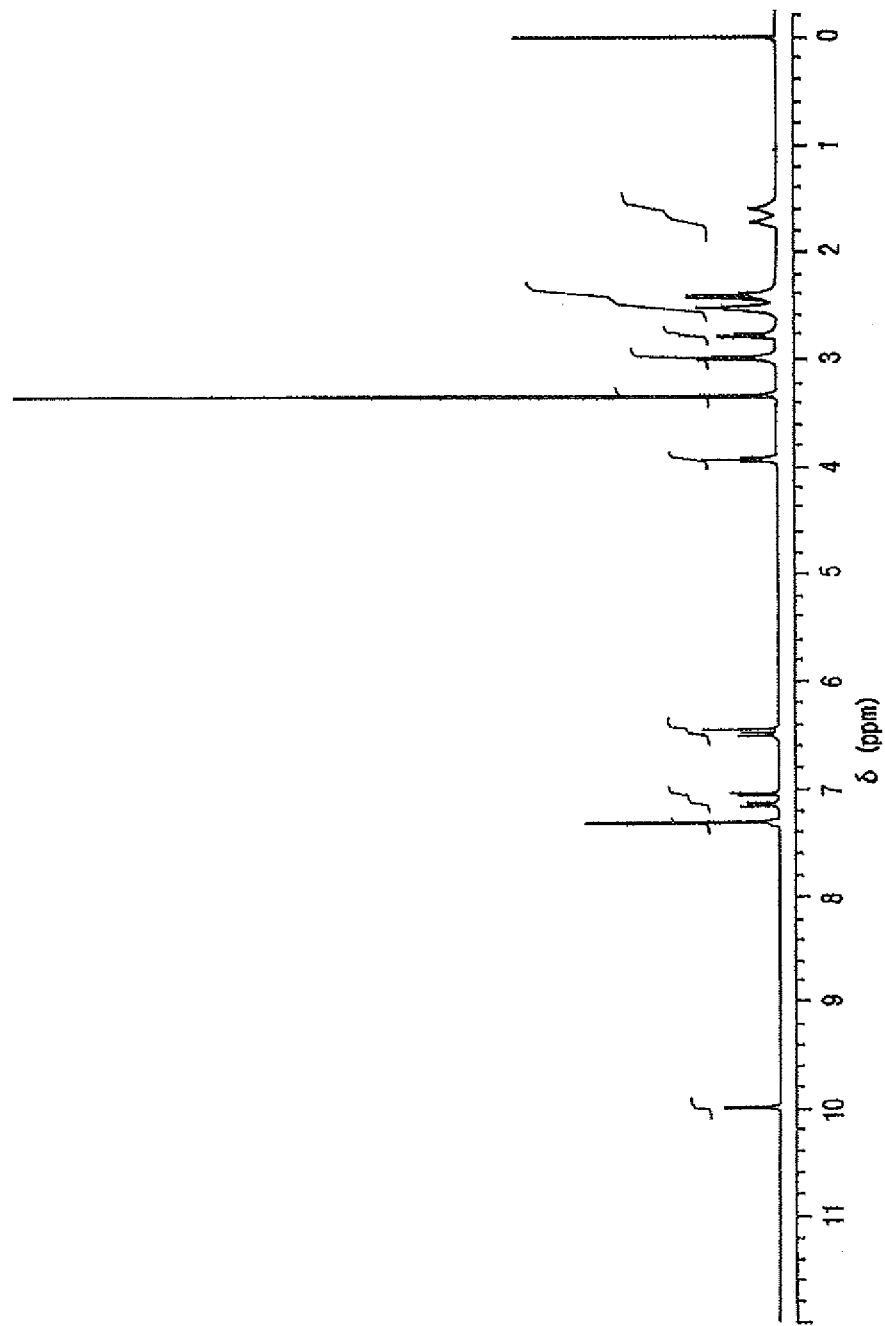
FIG. 2 shows the $^1$H-NMR spectrum for the aripiprazole hydrate (grains) of the present invention.

(2) It has an $^1$H-NMR spectrum which is substantially the same as the $^1$H-NMR spectrum (DMSO-$d_6$, TMS) shown in FIG. 2. Specifically, it has characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

Figure 3:
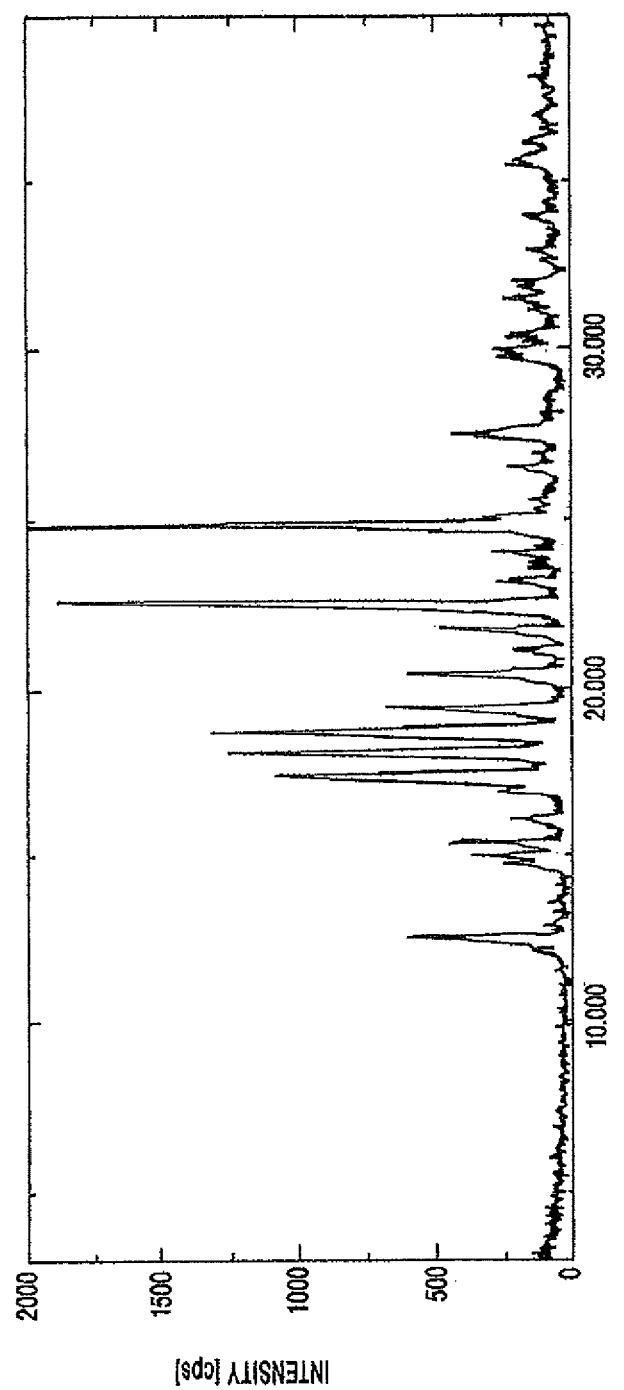
FIG. 3 shows the powder x-ray diffraction spectrum for the aripiprazole hydrate (grains) of the present invention.

(3) It has a powder x-ray diffraction spectrum which is substantially the same as the powder x-ray diffraction spectrum shown in FIG. 3. Specifically, it has characteristic peaks at 2θ=12.6°, 15.4°, 17.3°, 18.0°, 18.6°, 22.5° and 24.8°.

(4) It has clear infrared absorption bands at 2951, 2822, 1692, 1577, 1447, 1378, 1187, 963 and 784 cm$^{-1}$ on the IR (KBr) spectrum.

(5) It has a mean grain size of 50 μm or less.

Method of Manufacturing Aripiprazole Hydrate A

Aripiprazole Hydrate A is manufactured by milling conventional aripiprazole hydrate.

Conventional milling methods can be used to mill the aripiprazole hydrate. For example, the aripiprazole hydrate can be milled in a milling machine. A widely used milling machine can be used, such as an atomizer, pin mill, jet mill or ball mill. Of these, the atomizer is preferred.

Regarding the specific milling conditions when using an atomizer, a rotational speed of 5000-15000 rpm could be used for the main axis, for example, with a feed rotation of 10-30 rpm and a screen hole size of 1-5 mm.

The mean grain size of the Aripiprazole Hydrate A obtained by milling should normally be 50 μm or less, preferably 30 μm or less. Mean grain size can be ascertained by the grain size measurement method described hereinafter.

Grain Size Measurement: 0.1 g of the grains to be measured were suspended in a 20 ml n-hexane solution of 0.5 g soy lecithin, and grain size was measured using a size distribution meter (Microtraek HRA, Microtrack Co.).

Aripiprazole Anhydride Crystals

The aripiprazole anhydride crystals of the present invention have the physicochemical properties given in (6)-(10) below. These aripiprazole anhydride crystals are referred to hereinafter as "Aripiprazole Anhydride Crystals B".

Figure 4:
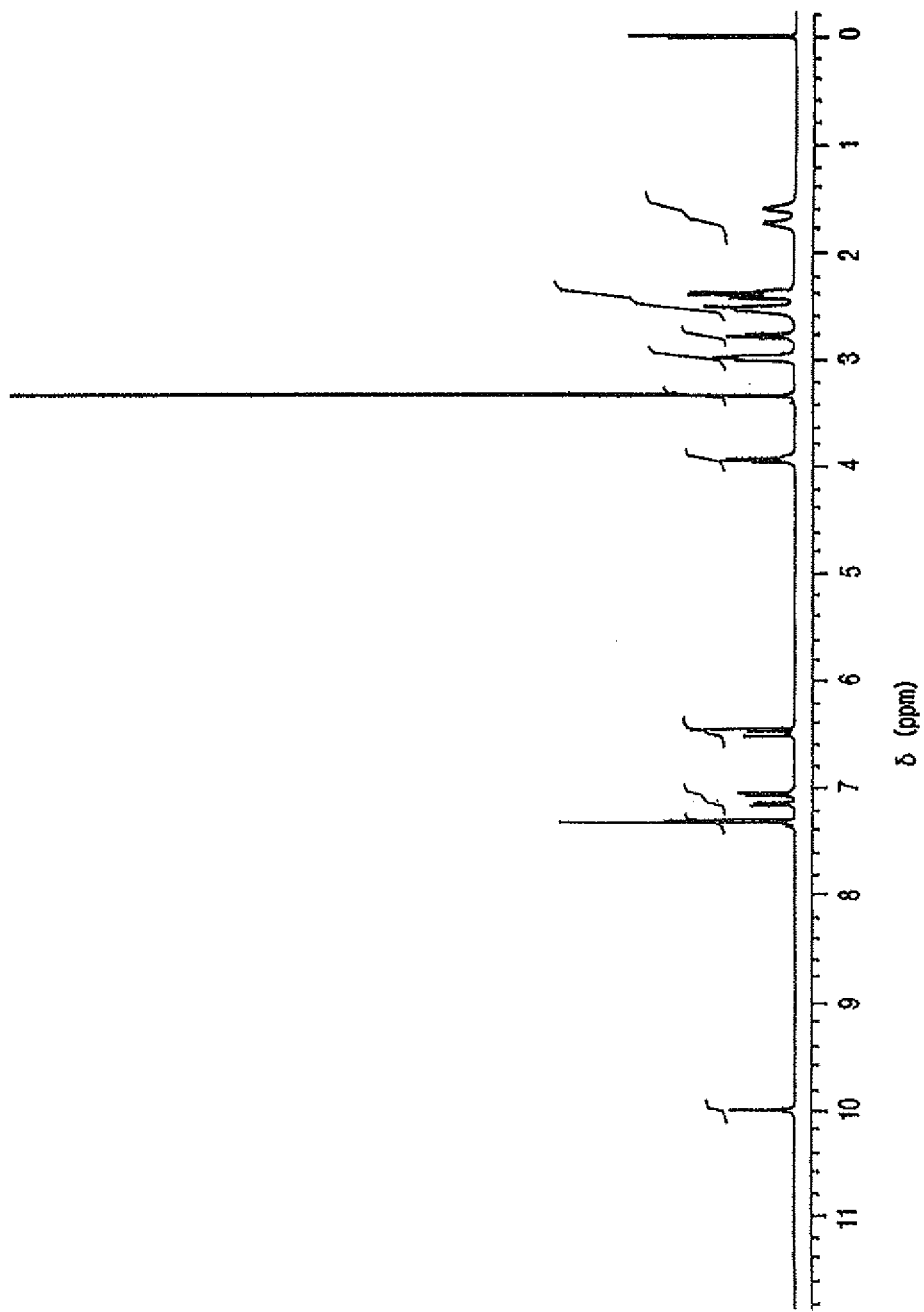
FIG. 4 shows the $^1$H-NMR spectrum data for the aripiprazole anhydride crystals of the present invention according to a further embodiment.

(6) They have an $^1$H-NMR spectrum which is substantially the same as the $^1$H-NMR spectrum (DMSO-$d_6$, TMS) shown in FIG. 4. Specifically, they have characteristic peaks at 1.55-1.63 ppm (m, 2H), 1.68-1.78 ppm (m, 2H), 2.35-2.46 ppm (m, 4H), 2.48-2.56 ppm (m, 4H+DMSO), 2.78 ppm (t, J=7.4 Hz, 2H), 2.97 ppm (brt, J=4.6 Hz, 4H), 3.92 ppm (t, J=6.3 Hz, 2H), 6.43 ppm (d, J=2.4 Hz, 1H), 6.49 ppm (dd, J=8.4 Hz, J=2.4 Hz, 1H), 7.04 ppm (d, J=8.1 Hz, 1H), 7.11-7.17 ppm (m, 1H), 7.28-7.32 ppm (m, 2H) and 10.00 ppm (s, 1H).

Figure 5:
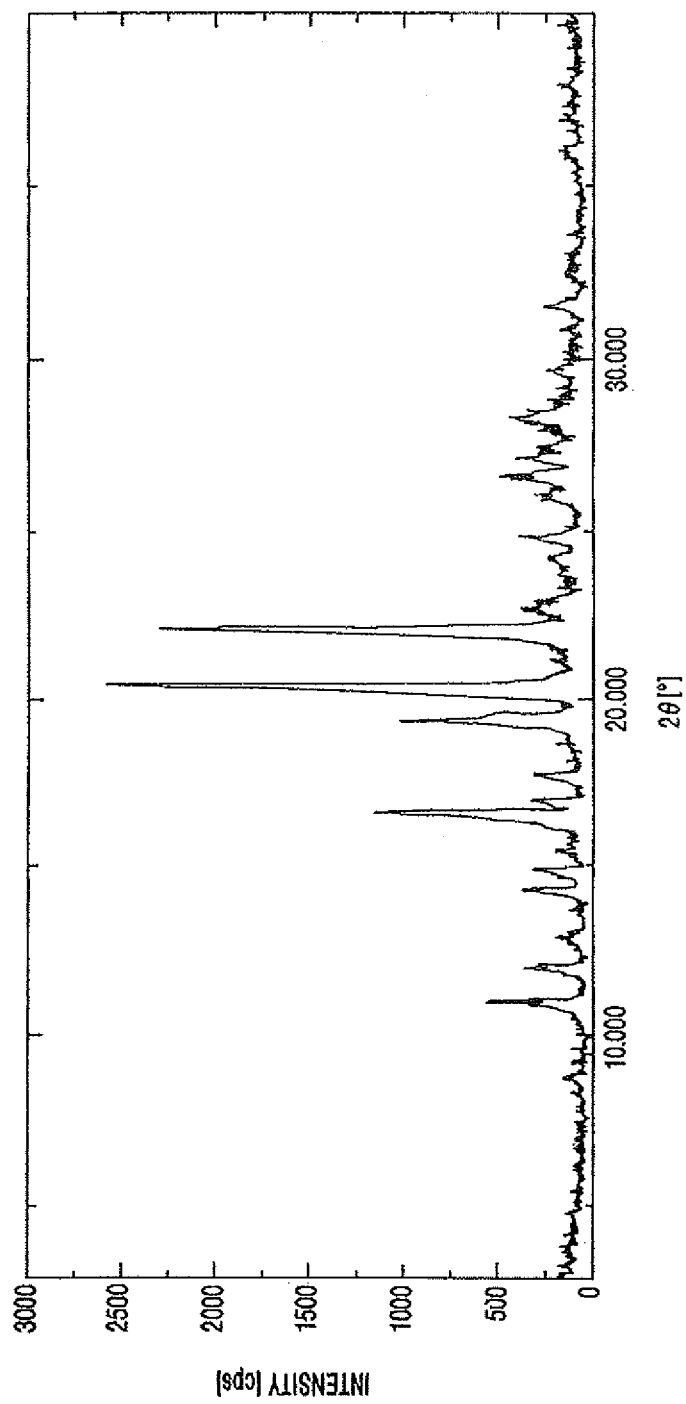
FIG. 5 shows the powder x-ray diffraction spectrum for the anhydride crystals of the present invention according to a further embodiment.

(7) They have a powder x-ray diffraction spectrum which is substantially the same as the powder x-ray diffraction spectrum shown in FIG. 5. Specifically, they have characteristic peaks at 2θ=11.0°, 16.6°, 19.3°, 20.3° and 22.1°.

(8) They have clear infrared absorption bands at 2945, 2812, 1678, 1627, 1448, 1377, 1173, 960 and 779 cm$^{-1}$ on the IR (KBr) spectrum.

(9) They exhibit an endothermic peak near about 141.5° C. in thermogravimetric/differential thermal analysis (heating rate 5° C./min).

(10) They exhibit an endothermic peak near about 140.7° C. in differential scanning calorimetry (heating rate 5° C./min).

Aripiprazole Anhydride Crystals B of the present invention have low hygroscopicity. For example, Aripiprazole Anhydride Crystals B of the present invention maintain a water content of 0.4% or less after 24 hours inside a dessicator set at a temperature of 60° C. and a humidity of 100%.

Well-known methods of measuring water content can be used as long as they are methods commonly used for measuring the water content of crystals. For example, a method such as the Karl Fischer method can be used.

Method of Manufacturing Aripiprazole Anhydride Crystals B

The Aripiprazole Anhydride Crystals B of the present invention are prepared for example by heating the aforementioned Aripiprazole Hydrate A at 90-125° C. The heating time is generally about 3-50 hours, but cannot be stated unconditionally since it differs depending on heating temperature. The heating time and heating temperature are inversely related, so that for example the heating time will be longer the lower the heating temperature, and shorter the higher the heating temperature. Specifically, if the heating temperature of Aripiprazole Hydrate A is 100° C., the heating time should normally be 18 hours or more or preferably about 24 hours. If the heating temperature of Aripiprazole Hydrate A is 120° C., on the other hand, the heating time can be about 3 hours. The Aripiprazole Anhydride Crystals B of the present invention can be prepared with certainty by heating Aripiprazole Hydrate A for about 18 hours at 100° C., and then heating it for about 3 hours at 120° C. The Aripiprazole Anhydride Crystals B of the present invention can also be obtained if the heating time is extended still further, but this is not economical.

Furthermore, the Aripiprazole Anhydride Crystals B of the present invention are prepared for example by heating conventional aripiprazole anhydride crystals at 90-125° C. The heating time is generally about 3-50 hours, but cannot be stated unconditionally since it differs depending on heating temperature. The heating time and heating temperature are inversely related, so that for example the heating time will be longer the lower the heating temperature, and shorter the higher the heating temperature. Specifically, if the heating temperature of the aripiprazole anhydride crystals is 100° C., the heating time can be about 4 hours, and if the heating temperature is 120° C. the heating time can be about 3 hours.

The aripiprazole anhydride crystals which are the raw material for preparing the Aripiprazole Anhydride Crystals B of the present invention are prepared for example by Method a or b below.

Method a:

Aripiprazole anhydride crystals are prepared by well-known methods, as by reacting 7-(4-bromobutoxy)-3,4-dihydrocarbostyril with 1-(2,3-dichlorophenyl) piperadine and recrystallizing the resulting raw aripiprazole crystals with ethanol as described in Example 1 of Japanese Unexamined Patent Publication No. 191256/1990.

13

Method b:

Aripirazole anhydride crystals are prepared by heating conventional aripiprazole hydrate at a temperature of at least 60° C. and less than 90° C. The heating time is generally about 1-30 hours, but cannot be stated unconditionally since it differs depending on heating temperature. The heating time and heating temperature are inversely related, so that for example the heating time will be longer the lower the heating temperature, and shorter the higher the heating temperature. Specifically, if the heating temperature of the aripiprazole hydrate is about 60° C., the heating time can be about 8 hours, while if the heating temperature is 80° C., the heating time can be about 4 hours.

The Method b is described in the Proceedings of the 4th Japanese-Korean Symposium on Separation Technology (Oct. 6-8, 1996).

Furthermore, the Aripiprazole Anhydride Crystals B of the present invention are prepared for example by heating conventional aripiprazole hydrate at 90-125° C. The heating time is generally about 3-50 hours, but cannot be stated unconditionally since it differs depending on heating temperature. The heating time and heating temperature are inversely related, so that for example the heating time will be longer the lower the heating temperature, and shorter the higher the heating temperature. Specifically, if the heating temperature of the aripiprazole hydrate is 100° C., the heating time can be about 24 hours, while if the heating temperature is 120° C., the heating time can be about 3 hours.

The aripiprazole hydrate which is the raw material for preparing the Aripiprazole Anhydride Crystals B of the present invention is prepared for example by Method c below.

Method c:

Aripiprazole hydrate is easily obtained by dissolving the aripiprazole anhydride crystals obtained by Method a above in a hydrous solvent, and heating and then cooling the resulting solution. Using this method, aripiprazole hydrate is precipitated as crystals in the hydrous solvent.

An organic solvent containing water is usually used as the hydrous solvent. The organic solvent should be one which is miscible with water, such as for example an alcohol such as methanol, ethanol, propanol or isopropanol, a ketone such as acetone, an ether such as tetrahydrofuran, dimethylformamide, or a mixture thereof, with ethanol being particularly desirable. The amount of water in the hydrous solvent can be 10-25% by weight of the solvent, or preferably close to 20% by weight.

As mentioned above, the Aripiprazole Anhydride Crystals B of the present invention are prepared by heating at 90-125° C. of said Aripiprazole Hydrate A, conventional aripiprazole anhydride crystals or conventional aripiprazole hydrate, and said Aripiprazole Hydrate A, conventional aripiprazole anhydride crystals or conventional aripiprazole hydrate may be used either individually or in combination.

The following examples used aripiprazole drug substance made by first milling the conventional hydrate of aripiprazole and then heating it to form the anhydrous form (anhydride B).

EXAMPLE 1

Flash-melt tablets were prepared as follows:

Intragranulation:

| Ingredient | Percent w/w | Mg. per tablet |
|---|---|---|
| Xylitol (300) Xylisorb | 26 | 52 |
| Avicel ® PH 102 | 12 | 24 |
| Calcium Silicate | 43.35 | 86.7 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |
| Acesulfame K | 2 | 4 |
| Magnesium stearate | 0.25 | 0.5 |
| Total weight | 92.75 | 185.5 |

The ingredients except for the magnesium stearate were blended in a commercial V-blender in geometric proportions for 5 minutes each until all were added. The magnesium stearate was then added and the mixture blended for an additional three minutes. The blended formulation was compacted at a pressure of 30-35 kgF/cm$^2$ in a commercial compactor equipped with an orifice such that the compacts therefrom are in the form of ribbons. The ribbons were passed through a 30 mesh (600 microns) screen to form stable granules of about 150 to 400 microns.

Extragranulation Ingredients:

| Ingredient | Percent w/w | Mg. per tablet |
|---|---|---|
| Intragranulation | 92.75 | 185.5 |
| Avicel ® PH 200 | 3 | 6 |
| Crospovidone | 4 | 8 |
| Magnesium stearate | 0.25 | 0.5 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.3 kP (3.5 SCU) and disintegrated in 10 seconds in 5 ml of water. The final blend formulation demonstrated excellent flow and was free of other problems such as chipping, capping and sticking. It has been found that utilizing Avicel® PH 102 for the intragranulation and Avicel® PH 200 for the extragranulation ingredient enhanced the quality of the resultant tablets.

EXAMPLE 2

Flash-melt tablets containing a combination of two grades of calcium silicate were prepared as follows:

Intragranulation:

| Ingredient | Percent w/w | Mg. per tablet |
|---|---|---|
| Xylitol (300) Xylisorb | 26 | 52 |
| Avicel ® PH 102 | 12 | 24 |
| Calcium Silicate (crystalline, alpha triclinic) | 33.35 | 66.7 |
| Hubersorb 600 NF (amorphous calcium silicate) | 10 | 20 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |

-continued

| Ingredient | Percent w/w | Mg. per tablet |
| --- | --- | --- |
| Acesulfame K | 2 | 4 |
| Magnesium stearate | 0.25 | 0.5 |
| Total weight | 92.75 | 185.5 |

The ingredients except for the magnesium stearate were blended in a commercial V-blender in geometric proportions for 5 minutes each until all were added. The magnesium stearate was added and the mixture blended for an additional three minutes. The blended formulation was compacted, and screened to form stable granules in accordance with the procedure of Example 1.

Extragranulation Ingredients:

| Ingredient | Percent w/w | Mg. per tablet |
| --- | --- | --- |
| Intragranulation | 92.75 | 185.5 |
| Avicel ® PH 200 | 3 | 6 |
| Crospovidone | 4 | 8 |
| Magnesium stearate | 0.25 | 0.5 |
| Total weight | 100 | 200 |

The intragranulation was placed in the blender and the Avicel® PH 200 and crospovidone added thereto and blended for live minutes. The magnesium stearate was then added and the mixture blended for an additional three minutes to form the final blend. Tablets compressed therefrom had a breaking force of 2.0 kP (3.1 SCU) and disintegrated in 10 seconds in 5 ml of water.

EXAMPLE 3

Flash-melt tablets containing aripiprazole, an antischizophrenic drug, were prepared as follows:

Intragranulation

| Ingredient | Percent w/w | Mg. per tablet |
| --- | --- | --- |
| Aripiprazole | 15 | 30 |
| Xylitol (300) Xylisorb | 25 | 50 |
| Avicel ® PH 102 | 6 | 12 |
| Calcium Silicate | 37 | 74 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |
| Acesulfame K | 2 | 4 |
| Magnesium stearate | 0.25 | 0.5 |
| Total weight | 94.4 | 188.8 |

The ingredients except for the magnesium stearate were blended in a commercial V-blender in geometric proportions for 5 minutes each until all were added. The magnesium stearate was added and the mixture blended for an additional three minutes. The blended formulation was compacted, and screened to form stable granules in accordance with the procedure of Example 1.

Extragranulation Ingredients:

| Ingredient | Percent w/w | Mg. per tablet |
| --- | --- | --- |
| Intragranulation | 94.4 | 188.8 |
| Avicel ® PH 200 | 1.1 | 2.2 |
| Crospovidone | 4 | 8 |
| Magnesium stearate | 0.5 | 1 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.0 kP (3.1 SCU) and disintegrated in 10 seconds in 5 ml of water.

EXAMPLE 4

Flash-melt tablets containing aripiprazole were prepared as follows:

Intragranulation:

| Ingredient | Percent w/w | Mg. per tablet |
| --- | --- | --- |
| Aripiprazole | 0.5 | 1 |
| Xylitol (300) Xylisorb | 27 | 54 |
| Avicel ® PH 102 | 12 | 24 |
| Calcium Silicate | 42 | 84 |
| Crospovidone | 3 | 6 |
| Amorphous silica | 2 | 4 |
| Aspartame | 2 | 4 |
| Wild cherry flavor | 0.15 | 0.3 |
| Tartaric acid | 2 | 4 |
| Acesulfame K | 2 | 4 |
| Magnesium stearate | 0.25 | 0.5 |
| Total weight | 92.9 | 185.8 |

The ingredients except for the magnesium stearate were blended in a commercial V-blender in geometric proportions for 5 minutes each until all were added. The magnesium stearate was added and the mixture blended for an additional three minutes. The blended formulation was compacted, and screened to form stable granules in accordance with the procedure of Example 1.

Extragranulation Ingredients:

| Ingredient | Percent w/w | Mg. per tablet |
| --- | --- | --- |
| Intragranulation | 92.9 | 185.8 |
| Avicel ® PH 200 | 2.6 | 5.2 |
| Crospovidone | 4 | 8 |
| Magnesium stearate | 0.5 | 1 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.3 kP (3.5 SCU) and disintegrated in 10 seconds in 5 ml of water.

EXAMPLE 5

Flash-melt tablets can be prepared containing the antiviral medicament entecavir as follows:

Intragranulation:

| Ingredient | Percent w/w | Mg. per tablet |
| --- | --- | --- |
| Entecavir | 1 | 2 |
| Xylitol (300) Xylisorb | 26 | 52 |
| Avicel ® PH 102 | 10 | 20 |
| Calcium Silicate | 45 | 90 |
| Crospovidone | 4 | 8 |
| Amorphous silica | 2 | 4 |
| Aspartame | 2 | 4 |
| Wild cherry flavor | 0.25 | 0.5 |
| Tartaric acid | 2 | 4 |
| Acesulfame K | 2 | 4 |
| Magnesium stearate | 0.25 | 0.5 |
| Total weight | 94.5 | 189 |

The ingredients except for the magnesium stearate were blended in a commercial V-blender in geometric proportions for 5 minutes each until all were added. The magnesium stearate was added and the mixture blended for an additional three minutes. The blended formulation was compacted, and screened to form stable granules in accordance with the procedure of Example 1.

Extragranulation Ingredients:

| Ingredient | Percent w/w | Mg. per tablet |
| --- | --- | --- |
| Intragranulation | 94.5 | 189 |
| Avicel ® PH 200 | 2 | 4 |
| Crospovidone | 3 | 6 |
| Magnesium stearate | 0.5 | 1 |
| Total weight | 100 | 200 |

The intragranulation was placed in the blender and the Avicel® PH 200 and crospovidone added thereto and blended for five minutes. The magnesium stearate was then added and the mixture blended for an additional three minutes to form the final blend. Tablets compressed therefrom had a breaking force of 2.3 kP (3.5 SCU) and disintegrated in 10 seconds in 5 ml of water. The percent w/w/ratios taught in this example can also be used to formulate a suitable formulation of the present invention comprising 0.1 mg of entecavir per unit dose.

EXAMPLE 6

Flash-melt tablets can be prepared containing the antibiotic medicament cefprozil as follows:

Intragranulation:

| Ingredient | Percent w/w | Mg. per tablet |
| --- | --- | --- |
| Cefzil | 25 | 125 |
| Xylitol (300) Xylisorb | 17 | 85 |
| Avicel ® PH 102 | 6 | 30 |
| Calcium Silicate | 35 | 175 |
| Crospovidone | 3 | 15 |
| Amorphous silica | 2. | 10 |
| Aspartame | 2 | 10 |
| Wild cherry flavor | 0.25 | 1.25 |
| Tartaric acid | 2 | 10 |
| Acesulfame K | 2 | 10 |
| Magnesium stearate | 0.25 | 1.25 |
| Total weight | 94.5 | 472.5 |

Blend the ingredients except for the magnesium stearate in a commercial V-blender in geometric proportions for 5 minutes each until all are added. Then add the magnesium stearate to the mixture prepared and mix for an additional three minutes. Then compact the blended formulation, and screen to form stable granules in accordance with the procedure of Example 1.

Extragranulation Ingredients:

| Ingredient | Percent w/w | Mg. per tablet |
| --- | --- | --- |
| Intragranulation | 94.5 | 472.5 |
| Avicel ® PH 200 | 2 | 10 |
| Crospovidone | 3 | 15 |
| Magnesium stearate | 0.5 | 2.5 |
| Total weight | 100 | 500 |

Place the intragranulation in the blender and add the Avicel® PH 200 and crospovidone thereto and blend for five minutes. Then add magnesium stearate to the mixture and blend for an additional three minutes to form the final blend. Compress tablets therefrom to have a breaking force of 2.5 kP (3.8 SCU) and a disintegration time of 10 seconds or less in 5 ml of water.

EXAMPLE 7

Flash-melt tablets can be prepared containing the antihypertensive medicament irbesartan as follows:

Intragranulation:

| Ingredient | Percent w/w | Mg. per tablet |
| --- | --- | --- |
| Irbesartan | 25 | 125 |
| Xylitol (300) Xylisorb | 17 | 85 |
| Avicel ® PH 102 | 6. | 30 |
| Calcium Silicate | 35 | 175 |
| Crospovidone | 3 | 15 |
| Amorphous silica | 2 | 10 |
| Aspartame | 2 | 10 |
| Wild cherry flavor | 0.25 | 1.25 |
| Tartaric acid | 2 | 10 |
| Acesulfame K | 2 | 10 |
| Magnesium stearate | 0.25 | 1.25 |
| Total weight | 94.5 | 472.5 |

Blend the ingredients except for the magnesium stearate in a commercial V-blender in geometric proportions for 5 minutes each until all are added. Then add the magnesium stearate to the mixture prepared and mix for an additional three minutes. Then compact the blended formulation, and screen to form stable granules in accordance with the procedure of Example 1.

Extragranulation Ingredients:

| Ingredient | Percent w/w | Mg. per tablet |
|---|---|---|
| Intragranulation | 94.5 | 472.5 |
| Avicel ® PH 20 | 2 | 10 |
| Crospovidone | 3 | 15 |
| Magnesium stearate | 0.5 | 2.5 |
| Total weight | 100 | 500 |

Place the intragranulation in the blender and add the Avicel® PH 200 and crospovidone thereto and blend for five minutes. Then add magnesium stearate to the mixture and blend for an additional three minutes to form the final blend. Compress tablets therefrom to have a breaking force of 2.5 kP (3.8 SCU) and a disintegration time of 10 seconds or less in 5 ml of water.

EXAMPLE 8

Flash-melt tablets can be prepared containing the quinolone antibiotic, des-Quinolone as follows:

Intragranulation:

| Ingredient | Percent w/w | Mg. per tablet |
|---|---|---|
| des-Quinolone | 20.0 | 100 |
| Xylitol (300) Xylisorb | 22.0 | 110 |
| Avicel ® PH 102 | 6.0 | 30 |
| Calcium Silicate | 35.0 | 175 |
| Crospovidone | 3.0 | 15 |
| Amorphous silica | 2.0 | 10 |
| Aspartame | 2.0 | 10 |
| Wild cherry flavor | 0.25 | 1.25 |
| Tartaric acid | | |
| Acesulfame K | | |
| Magnesium starate | 0.25 | |
| Total weight | | |

Blend the ingredients except for the magnesium stearate in a commercial V-blender in geometric proportions for 5 minutes each until all are added. Then add the magnesium stearate to the mixture prepared and mix for an additional three minutes. Then compact the blended formulation, and screen to form stable granules in accordance with the procedure of Example 1.

Extragranulation Ingredients:

| Ingredient | Percent w/w | Mg. per tablet |
|---|---|---|
| Intragranulation | 94.5 | 472.5 |
| Avicel ® PH 200 | 2.0 | 10.0 |
| Crospovidone | 3.0 | 15.0 |
| Magnesium stearate | 0.5 | 2.5 |
| Total weight | 100 | 500 |

Place the intragranulation in the blender and add the Avicel® PH 200 and crospovidone thereto and blend for five minutes. Then add magnesium stearate to the mixture and blend for an additional three minutes to form the final blend. Compress tablets therefrom to have a breaking force of 2.5 kP (3.8 SCU) and a disintegration time of 10 seconds or less in 5 ml of water.

EXAMPLE 9

Flash-melt tablets can be prepared containing the antibiotic gatifloxacin (Tequin®), as a taste masked co-precipitate (30% w/w active) to deliver 50 mg dose:

Intragranulation:

| Ingredient | Percent w/w | Mg. per tablet |
|---|---|---|
| Gatifloxacin:stearic acid co-precipitate | 33.3 | 166.7 |
| Xylitol (300) Xylisorb | 11.7 | 58.5 |
| Avicel ® PH 102 | 6.0 | 30 |
| Calcium Silicate | 32.0 | 160 |
| Crospovidone | 3.0 | 15 |
| Amorphous silica | 2.0 | 10 |
| Aspartame | 2.0 | 10 |
| Wild cherry flavor | 0.25 | 1.23 |
| Tartaric acid | 2.0 | 10 |
| Acesulfame K | 2.0 | 10 |
| Magnesium stearate | 0.25 | 1.25 |
| Total weight | 94.5 | 472.5 |

Blend the ingredients except for the magnesium stearate in a commercial V-blender in geometric proportions for 5 minutes each until all are added. Then add the magnesium stearate to the mixture prepared and mix for an additional three minutes. Then compact the blended formulation, and screen to form stable granules in accordance with the procedure of Example 1.

Extragranulation Ingredients:

| Ingredient | Percent w/w | Mg. per tablet |
|---|---|---|
| Intragranulation | 94.5 | 472.5 |
| Avicel ® PH 200 | 2.0 | 10.0 |
| Crospovidone | 3.0 | 15.0 |
| Magnesium stearate | 0.5 | 2.5 |
| Total weight | 100 | 500 |

Place the intragranulation in the blender and add the Avicel® PH 200 and crospovidone thereto and blend for five minutes. Then add magnesium stearate to the mixture and blend for an additional three minutes to form the final blend. Compress tablets therefrom to have a breaking force of 2.5 kP (3.8 SCU) and a disintegration time of 10 seconds or less in 5 ml of water.

EXAMPLE 10

Preparation of 2.5% W/W Aripiprazole Granulation for and 2 Mg and 5 Mg Tablets—Prototype II Intragranular Formulation:

| Ingredient | % w/w |
|---|---|
| Aripiprazole | 2.50 |
| Xylitol, NF (Xylisorb 300) | 21.15 |
| Microcrystalline Cellulose, NF (Avicel PH 102) | 12.0 |
| Calcium Silicate, NF | 42.0 |
| Crospovidone, NF (XL-10) | 3.0 |
| Silicon Dioxide, NF (previously referred to as Amorphous Silica) | 2.0 |
| Croscarmellose Sodium, NF | 3.0 |
| Aspartame, NF | 2.0 |
| Flavor Creme de Vanilla | 0.5 |
| Tartaric Acid, NF | 2 |
| Acesulfame K (E.P) | 2.0 |
| Magnesium stearate NF | 0.25 |
| Total | 92.40 |

Intragranular Blend Preparation:
1. V-blender is chosen (that operates at 50 rpm speed) for the mixing operation. In the first mixing step, aripiprazole is placed in between Xylitol and Avicel PH 102 mixed in the V-blender for 10 minutes.
2. In step 2, all other excipients are weighed out and placed in the V-blender from step 1. Deaggregation was performed where necessary. Mixing was done for 5 minutes.
3. Finally, 0.25% magnesium stearate was added and blended for 3 minutes.
4. For roller compaction Alexanderwerk WP 120×40 (roller compactor) or other similar equipment can be used with the following parameters:
   Screw speed: 25 rpm Rolls speed: 5 rpm; Vacuum pressure: −105 mbar
   Granulator: 75 rpm (fixed with top 4 mm screen and bottom 0.8 mm or 20# screen)
   Hydraulic pressure: 50 bar Post Dry Granulation Blend Preparation

| Ingredient | % w/w |
| --- | --- |
| Granulation from step 4 | 92.40 |
| Crospovidone, NF (XL-10) | 4.00 |
| Microcrystalline Cellulose, NF (Avicel ® PH 200) | 3.10 |
| Magnesium stearate, NF | 0.5 |
| Total | 100.00 |

1. Based on the yield from step 4 calculate the new batch size and place the intragranulation in the blender with the calculated amounts of Avicel® PH 200 and crospovidone and blend for 5 minutes.
2. Finally add the remaining amount of magnesium stearate and mix for 3 minutes.

2 mg tablets may have a green pigment blend incorporated in the extragranular portion above in a concentration of 0.3% w/w adjusted by replacing the same amount of Avicel PH 200, i.e. the amount of Avicel PH 200 will be 2.8% w/w.

5 mg tablets may have a blue aluminum lake incorporated in the extragranular portion above in a concentration of 0.3% w/w adjusted by replacing the same amount of Avicel PH 200, i.e. the amount of Avicel PH 200 will be 2.8% w/w.

Tablet Compression:
1. Using the granulation prepared above, 2 mg potency aripiprazole tablets can be prepared by compressing 80 mg weight tablets on any conventional tablet press that can produce tablets having a breaking force of 3.0 kP or 4.5 SCU.
2. Using the granulation prepared above, 5 mg potency aripiprazole tablets can be prepared by compressing 200 mg weight tablets on any conventional tablet press that can produce tablets having a breaking force of 3.0 kP or 4.5 SCU.

EXAMPLE 11

Preparation of 10% W/W Aripiprazole Granulation for and 10 Mg, 15 Mg, 20 Mg and 30 Mg Tablets—Prototype II Intragranular Formulation:

| Ingredient | % w/w |
| --- | --- |
| Aripiprazole | 10.00 |
| Xylitol, NF (Xylisorb 300) | 21.15 |
| Microcrystalline Cellulose, NF (Avicel PH 102) | 10.0 |
| Calcium Silicate, NF | 36.5 |
| Crospovidone, NF (XL-10) | 3.0 |
| Silicon Dioxide, NF (previously referred to as Amorphous Silica) | 3.0 |
| Croscarmellose Sodium, NF | 2.0 |
| Aspartame, NF | 2.0 |
| Flavor Creme de Vanilla | 0.5 |
| Tartaric Acid, NF | 2 |
| Acesulfame K (E.P) | 2.0 |
| Magnesium stearate NF | 0.25 |
| Total | 92.40 |

Intragranular Blend Preparation:
1. V-blender is chosen (that operates at 50 rpm speed) for the mixing operation. In the first mixing step, aripiprazole is placed in between Xylitol and Avicel PH 102 mixed in the V-blender for 10 minutes.
2. In step 2, all other excipients are weighed out and placed in the V-blender from step 1. Deaggregation was performed where necessary. Mixing was done for 5 minutes.
3. Finally, 0.25% magnesium stearate was added and blended for 3 minutes.
4. For roller compaction Alexanderwerk WP 120×40 (roller compactor) or other similar equipment can be used with the following parameters:
   Screw speed: 25 rpm Rolls speed: 5 rpm; Vacuum pressure: −105 mbar
   Granulator: 75 rpm (fixed with top 4 mm screen and bottom 0.8 mm or 20# screen)
   Hydraulic pressure: 50 bar Post Dry Granulation Blend Preparation

| Ingredient | % w/w |
| --- | --- |
| Granulation from step 4 | 92.40 |
| Crospovidone, NF (XL-10) | 4.00 |
| Microcrystalline Cellulose, NF (Avicel ® PH 200) | 3.10 |
| Magnesium stearate, NF | 0.5 |
| Total | 100.00 |

5. Based on the yield from step 4 calculate the new batch size and place the intragranulation in the blender with the calculated amounts of Avicel® PH 200 and crospovidone and blend for 5 minutes.
6. Finally add the remaining amount of magnesium stearate and mix for 3 minutes.
   10 mg tablets may have red iron oxide incorporated in the extragranular portion above in a concentration of 0.04% w/w adjusted by replacing the same amount of Avicel PH 200, i.e. the amount of Avicel PH 200 will be 3.06% w/w.

15 mg tablets may have yellow iron oxide incorporated in the extragranular portion above in a concentration of 0.3% w/w adjusted by replacing the same amount of Avicel PH 200, i.e. the amount of Avicel PH 200 will be 2.8% w/w.

20 mg tablets may be white in color and directly made from the formulation shown above.

30 mg tablets may have red iron oxide incorporated in the extragranular portion above in a concentration of 0.04% w/w adjusted by replacing the same amount of Avicel PH 200, i.e. the amount of Avicel PH 200 will be 3.06% w/w.

Tablet Compression:

1. Using the granulation prepared above, 10 mg potency aripiprazole tablets can be prepared by compressing 100 mg weight tablets on any conventional tablet press that can produce tablets having a breaking force of 3.0 kP or 4.5 SCU.
2. Using the granulation prepared above, 15 mg potency aripiprazole tablets can be prepared by compressing 150 mg weight tablets on any conventional tablet press that can produce tablets having a breaking force of 3.0 kP or 4.5 SCU.
3. Using the granulation prepared above, 20 mg potency aripiprazole tablets can be prepared by compressing 200 mg weight tablets on any conventional tablet press that can produce tablets having a breaking force of 3.0 kP or 4.5 SCU.
4. Using the granulation prepared above, 30 mg potency aripiprazole tablets can be prepared by compressing 300 mg weight tablets on any conventional tablet press that can produce tablets having a breaking force of 3.0 kP or 4.5 SCU.

Pharmacokinetic Evaluation of 5 Mg Flash-melt Tablets—Prototypes I and II in Healthy Human Subjects Open label, randomized, 2-period, 3 treatment control balanced crossover study involving 33 healthy volunteers was conducted. Each subject received one single 5 mg aripiprazole commercial tablet and a 5 mg dose of aripiprazole as either flash-melt Prototype I or flash-melt Prototype II (both from a 2.5% w/w granulation).

| | COMPOSITION (mg/tablet) | | | |
|---|---|---|---|---|
| | Prototype I | | Prototype II | |
| INGREDIENT | 5 mg[a] | % | 5 mg[b] | % |
| Aripiprazole | 5.0 | 2.50 | 5.0 | 2.50 |
| Calcium Silicate, NF | 84.0 | 42.00 | 84.0 | 42.00 |
| Crospovidone NF (XL-10) | 14.0 | 7.00 | 14.0 | 7.00 |
| Croscarmellose Sodium, NF | — | — | 6.0 | 3.00 |
| Silicon Dioxide, NF (Syloid) | 4.0 | 2.00 | 4.0 | 2.00 |
| Xylitol NF (Xylisorb ® 300) | 48.3 | 24.15 | 42.3 | 21.15 |
| Microcrystalline Cellulose NF (Avicel ® PH 102) | 24 | 12.00 | 24 | 12.00 |
| Microcrystalline Cellulose NF (Avicel ® PH 200) | 6.2 | 3.10 | 6.2 | 3.10 |
| Aspartame NF | 4.0 | 2.00 | 4.0 | 2.00 |
| Acesulfame Potassium | 4.0 | 2.00 | 4.0 | 2.00 |
| Creme de Vanilla (Natural & Artifical Flavors) | 1.0 | 0.50 | 1.0 | 0.50 |

-continued

| | COMPOSITION (mg/tablet) | | | |
|---|---|---|---|---|
| | Prototype I | | Prototype II | |
| INGREDIENT | 5 mg[a] | % | 5 mg[b] | % |
| Tartaric Acid NF | 4.0 | 2.00 | 4.0 | 2.00 |
| Magnesium Stearate NF | 1.5 | 0.75 | 1.5 | 0.75 |
| Total | 200 mg | 100.00 | 200 mg | 100.0 |

[a]Product Identification Number: 337039-A005-050;
[b]Product Identification Number: 337039-A005-051

The disintegration time for both prototypes in the mouth was less than 30 seconds. However, the two prototypes show different dissolution rates in in-vitro dissolution tests using USP dissolution testing methods. Hence, the goal of this study was to evaluate if these differences would affect in-vivo performance of the two prototypes.

The pharmacokinetic parameters from the clinical study are shown below:

| Formulation | Dose (mg) | N | Cmax (ng/mL) | Tmax* (h) | AUC(INF) [ng · h/mL] | F** (%) |
|---|---|---|---|---|---|---|
| Commercial Tablet | 5 | 33 | 21.4 (5.85) | 3 (1, 8) | 1393 (504) | — |
| Flashmelt Prototype I | 5 | 16 | 17.8 (3.85) | 4 (2, 12) | 1260 (474) | 99.7 (21.8) |
| Flashmelt Prototype II | 5 | 17 | 21.0 (4.40) | 4 (1.5, 8) | 1567 (677) | 105 (18.4) |

Based on statistical analysis for $C_{max}$ and AUC for the two prototypes (shown below) it was concluded that Prototype II is bioequivalent to the regular commercial aripiprazole tablets.

| Parameter | Ratio | N | Point Estimate | 90% CI |
|---|---|---|---|---|
| $C_{max}$ | B/A | 16 | 0.8809 | (0.7534, 1.0300) |
| | C/A | 17 | 0.9741 | (0.8767, 1.0823) |
| AUC (INF) | B/A | 16 | 0.9744 | (0.9107, 1.0491) |
| | C/A | 17 | 1.0141 | (0.9688, 1.0616) |
| AUC (0-T) | B/A | 16 | 0.9647 | (0.8941, 1.0408) |
| | C/A | 17 | 0.9979 | (0.9438, 1.0551) |

A = Aripiprazole 5 mg commercial tablet
B = Aripiprazole 5 mg flash-melt prototype I
C = Aripiprazole 5 mg flash-melt prototype II One Year Chemical Stability of 2 Mg and 30 Mg Potency Aripiprazole Flash-melt Tablets:

Shown below are the stability results for the 2 mg and 30 mg potency tablets placed on official IND stability testing. As seen from the results, only one degradant is seen that shows growth under accelerated conditions as well as at room temperature. This degradant has been identified as the N-oxide of aripiprazole (SFO-14094). The levels seen in the 2 mg tablets are significantly higher than those in the 30 mg tablets. Also, the N-oxide levels in the Prototype II formulation are significantly lower than those in the Prototype I formulation.

TABLE 1

Aripiprazole Flash-Melt Tablets; IND Stability Study -- 2-mg Prototype I

| | (%) calculated from the area under the chromatogram peak normalized for the area under the entire chromatogram | | | | | | | |
|---|---|---|---|---|---|---|---|---|
| Time Point and Storage Condition | Metabolite of aripiprazole/ oxidation product % RRT 0.91 | aripiprazole % RRT 1.00 | N-oxide of aripiprazole % RRT 1.08 | Unknown Impurities % RRT in ( ) | Total Impurities % | Potency (Result #1) mg/tab | Potency (Result #2) mg/tab | Potency (Reported Result) mg/tab |
| Initial | 0.06 | 99.94 | — | — | 0.06 | 2.01 | 1.97 | 1.99 |
| 1 day @ 25 C./75% RH (open) | 0.07 | 99.86 | 0.07 | — | 0.14 | 1.98 | NP | 1.98 |
| 4 days @ 25 C./HIL/UVA (exposed) | 0.06 | 99.81 | 0.13 | — | 0.19 | 1.97 | NP | 1.97 |
| 4 days @ 25 C./HIL/UVA (wrapped) | — | 99.95 | 0.05 | — | 0.05 | 2.02 | NP | 2.02 |
| 1 week @ 25 C./75% RH (open) | 0.09 | 99.73 | 0.18 | — | 0.27 | 1.96 | NP | 1.96 |
| 2 wks @ 25 C./HIL/UVA (exposed) | 0.08 | 99.71 | 0.15 | .06 (0.87) | 0.29 | 2.02 | NP | 2.02 |
| 2 wks @ 25 C./HIL/UVA (wrapped) | 0.05 | 99.90 | 0.05 | — | 0.10 | 1.98 | NP | 1.98 |
| 2 wks @ 25 C./60% RH (closed) | 0.05 | 99.95 | — | — | 0.05 | 2.03 | NP | 2.03 |
| 2 wks @ 25 C./75% RH (open) | 0.11 | 99.63 | 0.26 | — | 0.37 | 1.98 | NP | 1.98 |
| 4 wks @ 25 C./60% RH (closed) | 0.05 | 99.95 | — | — | 0.05 | 2.01 | NP | 2.01 |
| 4 wks @ 40 C./75% RH (closed) | 0.05 | 99.82 | 0.13 | — | 0.18 | 2.01 | NP | 2.01 |
| 4 wks @ 50 C. (closed) | 0.06 | 99.62 | 0.32 | — | 0.38 | 1.97 | NP | 1.97 |
| 13 wks @ 25 C./60% RH (closed) | 0.06 | 99.85 | 0.09 | — | 0.15 | 1.97 | NP | 1.97 |
| 13 wks @ 40 C./75% RH (closed) | 0.09 | 99.46 | 0.45 | — | 0.54 | 1.95 | NP | 1.95 |
| 13 wks @ 50 C. (closed) | 0.13 | 98.70 | 0.92 | 0.19 (0.38) | 1.30 | 1.95 | NP | 1.95 |
| 26 wks @ 25 C./60% RH (closed) | 0.05 | 99.81 | 0.14 | — | 0.19 | 2.05 | NP | 2.05 |
| 26 wks @ 40 C./75% RH (closed) | 0.11 | 99.18 | 0.71 | — | 0.82 | 2.03 | NP | 2.03 |
| 52 wks @ −15 C. (closed) | — | 100.00 | — | — | 0.00 | 2.05 | NP | 2.05 |
| 52 wks @ 25 C./60% RH (closed) | — | 99.77 | 0.23 | — | 0.23 | 1.97 | NP | 1.97 |

RRT = relative retention time (relative to the active compound, aripiprazole) during the chromatography analysis
Comments:
"—" indicates that no peak was detected or that the peak measured less than the reporting limit (<0.05 I.I.)
"NP" indicates, "Not Performed"

TABLE 2

Aripiprazole Flash-Melt Tablets; IND Stability Study -- 2-mg Prototype II

| | (%) calculated from the area under the chromatogram peak normalized for the area under the entire chromatogram | | | | | | | |
|---|---|---|---|---|---|---|---|---|
| Time Point and Storage Condition | Metabolite of aripiprazole/ oxidation product % RRT 0.91 | aripiprazole % RRT 1.00 | N-oxide of aripiprazole % RRT 1.08 | Unknown Impurities % RRT in ( ) | Total Impurities % | Potency (Result #1) mg/tab | Potency (Result #2) mg/tab | Potency (Reported Result) mg/tab |
| Initial | 0.05 | 99.95 | — | — | 0.05 | 2.05 | 2.04 | 2.05 |
| 1 day @ 25 C./75% RH (open) | 0.07 | 99.86 | 0.07 | — | 0.14 | 2.01 | NP | 2.01 |
| 4 days @ 25 C./HIL/UVA (exposed) | 0.06 | 99.86 | 0.08 | — | 0.14 | 2.00 | NP | 2.00 |
| 4 days @ 25 C./HIL/UVA (wrapped) | 0.06 | 99.89 | 0.06 | — | 0.11 | 2.00 | NP | 2.00 |
| 1 week @ 25 C./75% RH (open) | 0.08 | 99.80 | 0.12 | — | 0.20 | 2.00 | NP | 2.00 |
| 2 wks @ 25 C./HIL/UVA (exposed) | 0.09 | 99.74 | 0.12 | 0.06 (0.87) | 0.26 | 2.00 | NP | 2.00 |
| 2 wks @ 25 C./HIL/UVA (wrapped) | 0.05 | 99.95 | — | — | 0.05 | 2.02 | NP | 2.02 |
| 2 wks @ 25 C./60% RH (closed) | 0.06 | 99.89 | 0.05 | — | 0.11 | 2.00 | NP | 2.00 |
| 2 wks @ 25 C./75% RH (open) | 0.10 | 99.72 | 0.18 | — | 0.28 | 1.99 | NP | 1.99 |
| 4 wks @ 25 C./60% RH (closed) | 0.05 | 99.95 | — | — | 0.05 | 2.01 | NP | 2.01 |
| 4 wks @ 40 C./75% RH (closed) | 0.05 | 99.90 | 0.05 | — | 0.10 | 2.04 | NP | 2.04 |
| 4 wks @ 50 C. (closed) | 0.07 | 99.68 | 0.25 | — | 0.32 | 2.02 | NP | 2.02 |
| 13 wks @ 25 C./60% RH (closed) | 0.06 | 99.88 | 0.06 | — | 0.12 | 2.00 | NP | 2.00 |
| 13 wks @ 40 C./75% RH (closed) | 0.08 | 99.63 | 0.29 | — | 0.37 | 1.98 | NP | 1.98 |
| 13 wks @ 50 C. (closed) | 0.12 | 98.89 | 0.74 | 0.20 (0.38) | 1.11 | 1.98 | NP | 1.98 |
| 26 wks @ 25 C./60% RH (closed) | 0.06 | 99.86 | 0.08 | — | 0.14 | 2.06 | NP | 2.06 |
| 26 wks @ 40 C./75% RH (closed) | 0.16 | 99.29 | 0.55 | — | 0.71 | 2.02 | NP | 2.02 |
| 52 wks @ −15 C. (closed) | — | 100.00 | — | — | 0.00 | 2.01 | NP | 2.01 |
| 52 wks @ 25 C./60% RH (closed) | — | 99.89 | 0.11 | — | 0.11 | 2.02 | NP | 2.02 |

RRT = relative retention time (relative to the active compound, aripiprazole) during the chromatography analysis
Comments:
"—" indicates that no peak was detected or that the peak measured less than the reporting limit (<0.05 I.I.)
"NP" indicates, "Not Performed"

TABLE 3

Aripiprazole Flash-Melt Tablets; IND Stability Study -- 30-mg Prototype I (%) calculated from the area under the chromatogram peak normalized for the area under the entire chromatogram

| Time Point and Storage Condition | Metabolite of aripiprazole/ oxidation product % RRT 0.91 | aripiprazole % RRT 1.00 | N-oxide of aripiprazole % RRT 1.08 | Unknown Impurities % RRT in ( ) | Total Impurities % | Potency (Result #1) mg/tab | Potency (Result #2) mg/tab | Potency (Reported Result) mg/tab |
|---|---|---|---|---|---|---|---|---|
| Initial | 0.06 | 99.94 | — | — | 0.06 | 29.54 | 29.90 | 29.7 |
| 1 day @ 25 C./75% RH (open) | 0.07 | 99.88 | 0.05 | — | 0.12 | 28.98 | NP | 29.0 |
| 4 days @ 25 C./HIL/UVA (exposed) | 0.05 | 99.89 | 0.06 | — | 0.11 | 29.39 | NP | 29.4 |
| 4 days @ 25 C./HIL/UVA (wrapped) | 0.06 | 99.89 | 0.05 | — | 0.11 | 29.41 | NP | 29.4 |
| 1 week @ 25 C./75% RH (open) | 0.10 | 99.82 | 0.08 | — | 0.18 | 28.24 | 29.30 | 29.3* |
| 2 wks @ 25 C./HIL/UVA (exposed) | 0.05 | 99.85 | 0.10 | — | 0.15 | 29.52 | NP | 29.5 |
| 2 wks @ 25 C./HIL/UVA (wrapped) | 0.05 | 99.89 | 0.06 | — | 0.11 | 29.98 | NP | 30.0 |
| 2 wks @ 25 C./60% RH (closed) | 0.06 | 99.87 | 0.07 | — | 0.13 | 29.77 | NP | 29.8 |
| 2 wks @ 25 C./75% RH (open) | 0.08 | 99.81 | 0.11 | — | 0.19 | 29.74 | NP | 29.7 |
| 4 wks @ 25 C./60% RH (closed) | 0.05 | 99.95 | — | — | 0.05 | 29.08 | NP | 29.1 |
| 4 wks @ 40 C./75% RH (closed) | — | 99.95 | 0.05 | — | 0.05 | 29.37 | NP | 29.4 |
| 4 wks @ 50 C. (closed) | 0.06 | 99.87 | 0.07 | — | 0.13 | 29.70 | NP | 29.7 |
| 13 wks @ 25 C./60% RH (closed) | 0.06 | 99.90 | 0.05 | — | 0.10 | 29.73 | NP | 29.7 |
| 13 wks @ 40 C./75% RH (closed) | 0.06 | 99.85 | 0.09 | — | 0.15 | 29.89 | NP | 29.9 |
| 13 wks @ 50 C. (closed) | 0.06 | 99.77 | 0.17 | — | 0.23 | 29.74 | NP | 29.7 |
| 26 wks @ 25 C./60% RH (closed) | 0.05 | 99.91 | 0.04 | — | 0.09 | 29.26 | NP | 29.3 |
| 26 wks @ 40 C./75% RH (closed) | 0.06 | 99.81 | 0.13 | — | 0.19 | 29.41 | NP | 29.4 |
| 52 wks @ −15 C. (closed) | 0.05 | 99.95 | — | — | 0.05 | 29.70 | NP | 29.7 |
| 52 wks @ 25 C./60% RH (closed) | 0.06 | 99.88 | 0.06 | — | 0.12 | 29.90 | NP | 29.9 |

RRT = relative retention time (relative to the active compound, aripiprazole) during the chromatography analysis
Comments:
"—" indicates that no peak was detected or that the peak measured less than the reporting limit (<0.05 I.I.)
"NP" indicates, "Not Performed"
*Only Result 2 is reported (29.3); Result 1 (28.2) is believed to be low because of incomplete extraction.

TABLE 4

Aripiprazole Flash-Melt Tablets; IND Stability Study - 30-mg Prototype II (%) calculated from the area under the chromatogram peak normalized for the area under the entire chromatogram

| Time Point and Storage Condition | Metabolite of aripiprazole/ oxidation product % RRT 0.91 | aripiprazole % RRT 1.00 | N-oxide of aripiprazole % RRT 1.08 | Unknown Impurities % RRT in ( ) | Total Impurities % | Potency (Result #1) mg/tab | Potency (Result #2) mg/tab | Potency (Reported Result) mg/tab |
|---|---|---|---|---|---|---|---|---|
| Initial | 0.05 | 99.95 | — | — | 0.05 | 28.86 | 29.78 | 29.3 |
| 1 day @ 25 C./75% RH (open) | 0.07 | 99.88 | 0.05 | — | 0.12 | 29.01 | NP | 29.0 |
| 4 days @ 25 C./HIL/UVA (exposed) | 0.05 | 99.91 | 0.05 | — | 0.09 | 29.20 | NP | 29.2 |
| 4 days @ 25 C./HIL/UVA (wrapped) | 0.06 | 99.94 | — | — | 0.06 | 29.54 | NP | 29.5 |
| 1 week @ 25 C./75% RH (open) | 0.08 | 99.86 | 0.06 | — | 0.14 | 28.94 | NP | 28.9 |
| 2 wks @ 25 C./HIL/UVA (exposed) | 0.05 | 99.87 | 0.07 | — | 0.13 | 29.23 | NP | 29.2 |
| 2 wks @ 25 C./HIL/UVA (wrapped) | 0.05 | 99.95 | — | — | 0.05 | 29.45 | NP | 29.5 |
| 2 wks @ 25 C./60% RH (closed) | 0.05 | 99.95 | — | — | 0.05 | 29.02 | NP | 29.0 |
| 2 wks @ 25 C./75% RH (open) | 0.07 | 99.86 | 0.07 | — | 0.14 | 29.79 | NP | 29.8 |
| 4 wks @ 25 C./60% RH (closed) | 0.05 | 99.95 | — | — | 0.05 | 29.53 | NP | 29.5 |
| 4 wks @ 40 C./75% RH (closed) | 0.05 | 99.95 | — | — | 0.05 | 29.14 | NP | 29.1 |
| 4 wks @ 50 C. (closed) | 0.05 | 99.90 | 0.05 | — | 0.10 | 29.68 | NP | 29.7 |
| 13 wks @ 25 C./60% RH (closed) | 0.05 | 99.95 | — | — | 0.05 | 30.145 | NP | 30.1 |
| 13 wks @ 40 C./75% RH (closed) | 0.06 | 99.88 | 0.06 | — | 0.12 | 29.80 | NP | 29.8 |
| 13 wks @ 50 C. (closed) | 0.07 | 99.83 | 0.10 | — | 0.17 | 30.14 | NP | 30.1 |
| 26 wks @ 25 C./60% RH (closed) | 0.05 | 99.95 | — | — | 0.05 | 29.76 | NP | 29.8 |
| 26 wks @ 40 C./75% RH (closed) | 0.05 | 99.87 | 0.07 | — | 0.13 | 28.98 | NP | 29.0 |

TABLE 4-continued

Aripiprazole Flash-Melt Tablets; IND Stability Study - 30-mg Prototype II

| | (%) calculated from the area under the chromatogram peak normalized for the area under the entire chromatogram | | | | | | | |
|---|---|---|---|---|---|---|---|---|
| Time Point and Storage Condition | Metabolite of aripiprazole/ oxidation product % RRT 0.91 | aripiprazole % RRT 1.00 | N-oxide of aripiprazole % RRT 1.08 | Unknown Impurities % RRT in ( ) | Total Impurities % | Potency (Result #1) mg/tab | Potency (Result #2) mg/tab | Potency (Reported Result) mg/tab |
| 52 wks @ −15 C. (closed) | 0.05 | 99.95 | — | — | 0.05 | 29.14 | NP | 29.1 |
| 52 wks @ 25 C./60% RH (closed) | 0.07 | 99.93 | — | — | 0.07 | 30.17 | NP | 30.2 |

RRT = relative retention time (relative to the active compound, aripiprazole) during the chromatography analysis
Comments:
"—" indicates that no peak was detected or that the peak measured less than the reporting limit (<0.05 I.I.)
"NP" indicates, "Not Performed"

We claim:

1. A flash-melt pharmaceutical dosage form comprising a medicament, a superdisintegrant, a dispersing agent and a binder,
    wherein said medicament is aripiprazole, wherein said dispersing agent is calcium silicate,
    wherein said superdisintegrant is selected from the group of crospovidone and croscarmellose sodium, and
    wherein the flash-melt pharmaceutical dosage form dissolves or disintegrates in the mouth of a patient in less than one minute.

2. A flash-melt pharmaceutical dosage form according to claim 1, wherein said dispersing agent is present in an amount ranging from about 20 to about 70 percent by weight based on the total weight of said dosage form.

3. A flash-melt pharmaceutical dosage form according to claim 1, wherein said dispersing agent is present in an amount ranging from about 35 to about 45 percent by weight based on the total weight of said dosage form.

4. A flash-melt pharmaceutical dosage form according to claim 1, wherein said calcium silicate is orth-, meta- or alpha triclinic-calcium silicate.

5. A flash-melt pharmaceutical dosage form according to claim 1 wherein said calcium silicate is comprised of a combination of alpha triclinic-calcium silicate and at least one other pharmaceutical grade of calcium silicate wherein said alpha triclinic-calcium silicate comprises from about 10 percent to about 90 percent by weight of said combination.

6. A flash-melt pharmaceutical dosage form according to claim 1, wherein said medicament is present in an amount of not more than about 30 percent by weight based on the total weight of said dosage form.

7. A flash-melt pharmaceutical dosage form according to claim 1, wherein said medicament is present in an amount of not more than about 15 percent by weight based on the total weight of said dosage form.

8. A flash-melt pharmaceutical dosage form according to claim 1, wherein said superdisintegrant is present in an amount ranging from about 8 to about 12 percent by weight based on the total weight of said dosage form.

9. A flash-melt pharmaceutical dosage form according to claim 1, wherein said superdisintegrant is present in an amount ranging from about 9 to about 10 percent by weight based on the total weight of said dosage form.

10. A flash-melt pharmaceutical dosage form according to claim 1, wherein said crospovidone is present in an amount ranging from about 6 to about 8 percent by weight based on the total weight of said dosage form and said croscarmellose sodium is present in an amount ranging from about 2 to about 4 percent by weight based on the total weight of said dosage form.

11. A flash-melt pharmaceutical dosage form according to claim 1 further comprising a distributing agent.

12. A flash-melt pharmaceutical dosage form according to claim 11, wherein said distributing agent-is present in an amount ranging from about 1 to about 10 percent by weight based on the total weight of said dosage form.

13. A flash melt pharmaceutical dosage form according to claim 12, wherein said distributing agent is present in an amount ranging from about 1.5 to about 3 percent by weight based on the total weight of said dosage form.

14. A flash-melt pharmaceutical dosage form according to claim 13 wherein said distributing agent is amorphous silica, fumed silica, diatomaceous earth, talc, kaolin or magnesium aluminum trisilicate.

15. A flash-melt pharmaceutical dosage form according to claim 1 wherein said binder is microcrystalline cellulose, hydroxypropyl cellulose, ethyl cellulose, lactose, mannitol or calcium phosphate.

16. A flash-melt pharmaceutical dosage form comprising a medicament, a superdisintegrant, a dispersing agent, a distributing agent and a binder,
    wherein said medicament is aripiprazole which is present in an amount of not more than about 30 percent by weight based on the total weight of said dosage form, said dispersing agent is calcium silicate having a surface area of 1.0 $m^2$/gm to 210 $m^2$/gm, bulk density of 0.075 g/cc to 0.90 g/cc, true density of 1.70 g/cc to 2.90 g/cc and volatile content of less than 1 percent to 14 percent w/w and which is present in an amount ranging from about 35 to about 45 percent by weight based on the total weight of said dosage form, said superdisintegrant is crospovidone and croscarmellose sodium, said crospovidone is present in an amount ranging from about 6 to about 8 percent by weight based on the total weight of said dosage form and said croscarmellose sodium is present in an amount ranging from about 2 to about 4 percent by weight based on the total weight of said dosage form,
    wherein said distributing agent is amorphous silica, fumed silica, diatomaceous earth, talc, kaolin or magnesium aluminum trisilicate which is present in an amount ranging from about 1 to about 10 percent by weight based on the total weight of said dosage form, and wherein the flash-melt pharmaceutical dosage form dissolves or disintegrates in the mouth of a patient in less than one minute.

17. A flash melt pharmaceutical dosage form comprising a medicament, a superdisintegrant, a dispersing agent, a distributing agent and a binder,
   wherein said medicament is aripiprazole which is present in an amount of not more than about 30 percent by weight based on the total weight of said dosage form, said dispersing agent is calcium silicate having a surface area of 1.0 m$^2$/gm to 210 m$^2$/gm, bulk density of 0.075 g/cc to 0.90 g/cc, true density of 1.70 g/cc to 2.90 g/cc and volatile content of less than 1 percent to 14 percent w/w and which is present in an amount ranging from about 35 to about 45 percent by weight based on the total weight of said dosage form, said superdisintegrant is crospovidone and croscarmellose sodium, wherein said crospovidone is present in an amount ranging from about 7 percent by weight based on the total weight of said dosage form and wherein said croscarmellose is present in an amount ranging from about 3 percent by weight based on the total weight of said dosage form,
   wherein said distributing agent is amorphous silica, fumed silica, diatomaceous earth, talc, kaolin or magnesium aluminum trisilicate and is present in an amount ranging from about 10 to about 50 percent by weight basded on the total weight of said dosage form, and
   wherein the flash-melt pharmaceutical dosage form dissolves or disintegrates in the mouth of a patient in less than one minute.

18. A flash-melt pharmaceutical dosage form comprising a medicament, a superdisintegrant, a dispersing agent, a distributing agent and a binder,
   wherein said medicament is aripiprazole which is present in an amount of not more than about 20 percent by weight based on the total weight of said dosage form, said dispersing agent is calcium silicate having a surface area of 1.0 m$^2$/gm to 210 m$^2$/gm, bulk density of 0.075 g/cc to 0.90 g/cc, true density of 1.70 g/cc to 2.90 g/cc and volatile content of less than 1 percent to 14 percent w/w and which is present in an amount ranging from about 35 to about 45 percent by weight based on the total weight of said dosage form, said superdisintegrant is crospovidone and croscarmellose sodium, wherein said crospovidone is present in an amount ranging from about 7 percent by weight based on the total weight of said dosage form and wherein said croscarmellose is present in an amount ranging from about 3 percent by weight based on the total weight of said dosage form,
   wherein said distributing agent is amorphous silica, fumed silica, diatomaceous earth, talc, kaolin or magnesium aluminum trisilicate and is present in an amount ranging from about 10 to about 50 percent by weight based on the total weight of said dosage form, and
   wherein the flash-melt pharmaceutical dosage form dissolves or disintegrates in the mouth of a patient in less than one minute.

19. A flash-melt pharmaceutical dosage form comprising a medicament, a superdisintegrant, a dispersing agent, a distributing agent and a binder,
   wherein said medicament is aripiprazole which is present in an amount of not more than about 10 percent by weight based on the total weight of said dosage form, said dispersing agent is calcium silicate having a surface area of 1.0 m$^2$/gm to 210 m$^2$/gm, bulk density of 0.075 g/cc to 0.90 g/cc, true density of 1.70 g/cc to 2.90 g/cc and volatile content of less than 1 percent to 14 percent w/w and which is present in an amount ranging from about 35 to about 45 percent by weight based on the total weight of said dosage form, said superdisintegrant is crospovidone and croscarmellose sodium,
   wherein said crospovidone is present in an amount ranging from about 7 percent by weight based on the total weight of said dosage form and wherein said croscarmellose sodium is present in an amount ranging from about 3 percent by weight based on the total weight of said dosage form, and
   wherein the flash-melt pharmaceutical dosage form dissolves or disintegrates in the mouth of a patient in less than one minute.

20. A flash-melt pharmaceutical dosage form comprising a medicament, a superdisintegrant, a dispersing agent, a distributing agent and a binder,
   wherein said medicament is aripiprazole which is present in an amount of not more than about 5 percent by weight based on the total weight of said dosage form, said dispersing agent is calcium silicate having a surface area of 1.0 m$^2$/gm to 210 m$^2$/gm, bulk density of 0.075 g/cc to 0.90 g/cc, true density of 1.70 g/cc to 2.90 g/cc and volatile content of less than 1 percent to 14 percent w/w and is present in an amount ranging from about 35 to about 45 percent by weight based on the total weight of said dosage form, said superdisintegrant is crospovidone and croscarmellose sodium,
   wherein said crospovidone is present in an amount ranging from about 7 percent by weight based on the total weight of said dosage form and wherein said croscarmellose is present in an amount ranging from about 3 percent by weight based on the total weight of said dosage form, and
   wherein the flash-melt pharmaceutical dosage form dissolves or disintegrates in the mouth of a patient in less than one minute.

* * * * *